United States Patent
Jegla et al.

(10) Patent No.: US 6,994,968 B1
(45) Date of Patent: Feb. 7, 2006

(54) BK BETA SUBUNITS OF SLO FAMILY POTASSIUM CHANNELS

(75) Inventors: Timothy James Jegla, Durham, NC (US); Alan Wickenden, Cary, NC (US); Yi Liu, Cary, NC (US)

(73) Assignee: Icagen, Inc., Durham, NC (US)

( * ) Notice: Subject to any disclaimer, the term of this patent is extended or adjusted under 35 U.S.C. 154(b) by 0 days.

(21) Appl. No.: 09/914,053

(22) PCT Filed: Feb. 22, 2000

(86) PCT No.: PCT/US00/04441

§ 371 (c)(1),
(2), (4) Date: Apr. 3, 2002

(87) PCT Pub. No.: WO00/50444

PCT Pub. Date: Aug. 31, 2000

Related U.S. Application Data

(60) Provisional application No. 60/163,367, filed on Nov. 3, 1999, provisional application No. 60/121,224, filed on Feb. 23, 1999.

(51) Int. Cl.
*C12Q 1/68* (2006.01)
*C12P 21/06* (2006.01)
*C07K 14/00* (2006.01)

(52) U.S. Cl. .................... 435/6; 435/69.1; 435/41; 530/350; 800/8; 800/14

(58) Field of Classification Search ............ 435/6, 435/69.1, 41; 800/8, 14; 530/350
See application file for complete search history.

(56) References Cited

U.S. PATENT DOCUMENTS 5,526,281 A 6/1996 Chapman et al.
5,680,331 A 10/1997 Blaney et al.

FOREIGN PATENT DOCUMENTS

EP 0 936 271 A1 8/1999
WO WO 200105828 A1 * 1/2001

OTHER PUBLICATIONS

Bowie et.al., Science 247:1306-1310, 1990.*
Wells, Biochemistry 29:8509-8517, 1990.*
Wang et al. Nuc. Acids Res. 27: 4609-4618, 1999.*
Wigley et al. Reprod Fert Dev 6: 585-588, 1994.*
Campbell et al. Theriogenology 47(1): 63-72, 1997.*
Phillips, A., J Pharm Pharmacology 53: 1169-1174, 2001.*
Wallner et al. Proc. Natl. Acad. Sci. USA 96: 4137-4142, 1999.*
Riazi et al., "Identification of a putative regulatory subunit of a calcium-activated potassium channel in the dup(3q) syndrome region and relatred sequence on 22q11.2," *Genomics*, Nov. 1999, vol. 62, No. 1, Abstract only; USA.
Wallner et al., "Molecular basis of fst inactivation in voltage and Ca2+-activated K+channels: a transmembrane beta-subunit homolog," *Proc. Natl. Acad. Sci.*, Mar. 1999, vol. 96, pp. 4137-4142; USA.
Rettig et al., "Inactivation properties of voltage-gated K+channels altered by presence of beta-subunit," *Nature* May 26, 1994, vol. 369, pp. 289-294; USA.
Rhodes et al., Voltage-gated K+channel beta subunits: expression and distribution of KvB1 and KvB2 in adult rat brain. *J. Neurosc.* Aug. 15, 1996, vol. 16, No. 16, pp. 4846-4860; USA.

* cited by examiner

*Primary Examiner*—Janet Andres
*Assistant Examiner*—Gyan Chandra
(74) *Attorney, Agent, or Firm*—Townsend and Townsend and Crew LLP

(57) ABSTRACT

The invention provides isolated nucleic acid and amino sequences of BK beta 2, BK beta 3, and BK beta 4, antibodies to the BK beta subunits, methods of detecting the BK beta subunits, methods of screening for modulators of Slo family potassium channels comprising BK beta subunits.

6 Claims, 8 Drawing Sheets

```
                                          MAKLRVAYEYTEAEDKSI              BKB3
                                          MVKKLVMAQKRGETRAL               BKB1
  1         MSIWTSGRTSSSYRHDEKRNIYQKIRDHDLLDKRKTVTALKAGEDRAI               BKB4
  1                          MTAFPASGKKRETDYSDGDPLDVHKRLPSSTGEDRAV         BKB2

19  RLGLFLIISGVVSLEIFGFCWLSPALQDLQATEANCTVLSVQQIGEVFECTFTCGADC            BKB3
 18  CLGVIMVVCAVITYYIFLVTIFTVLPLYQKSVWTQESKCHLIETNIRDQ EE   LKG            BKB1
 49  LLGLAMMVCSIMMYFLLGITLLRSYMQSVWTEESQCTLLNASITET FMCSFSCGPDC            BKB4
 38  MLGFAMMGFSVLMFFLLGITILKPFMISIQREESTCTAIHTDIMDDWLDCAFTCGVHC            BKB2

77  RGTSQYPCVQVYVNNSESNSRALIHSDEHQLLTNPKCSYIPPCKRENQKNLESVMNWQ             BKB3
 69  KKVPQYPCL    WVNVSAAGRWAMYHTEDTRDQNQCSYIPGSVDNYQTARADVEKVR             BKB1
106  WKLSQYPCLQVYVNLTSSGEKILLYHTEETIKINQKCSYIPKCGKNFEESMSIVNVM             BKB4
 96  HGQGKYPCLQVFVNLSHPGDKALLHYNEEAVQINPKCFYTPKCHQDRNDLLNSALDIK            BKB2

135  QYWKDEIGSQPFTCYFNQHQRPDDVLIHRTHDEIVLLHCFLWPLVTFVVGVLIVVLTI            BKB3
125  AKFQEQQ    VEYCFSAPRGNETSVLFQRLYGPQALLFSLFWPTFLLTGGLLIFAMVK           BKB1
164  ENFRKYQ    HEFSCYSDPEGNQKSVILTKLYSSNVLFHSLFWPTCMMAGGVAIVAMVK          BKB4
154  EFEDHKNGT  PESCFYSPASQSEDVILIKKYDQMAIFHCLFWPSLTLLGGALIVGMVR           BKB2

193  CAKSTAVKAEAMKKRKFS                                                    BKB3
180  SNQYLSIDAAQK                                                          BKB1
219  LTQYLSLICERIQRINR                                                     BKB4
211  LTQHLSLLCEKYSTVVRDEVGGKVPYIEQHQFKLCIMRRSKGRAEKS                       BKB2
```

*FIG. 1.*

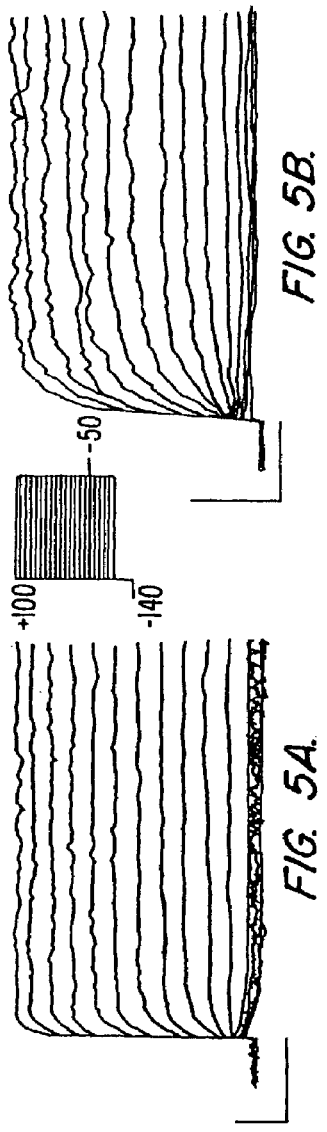
FIG. 5B.
FIG. 5A.
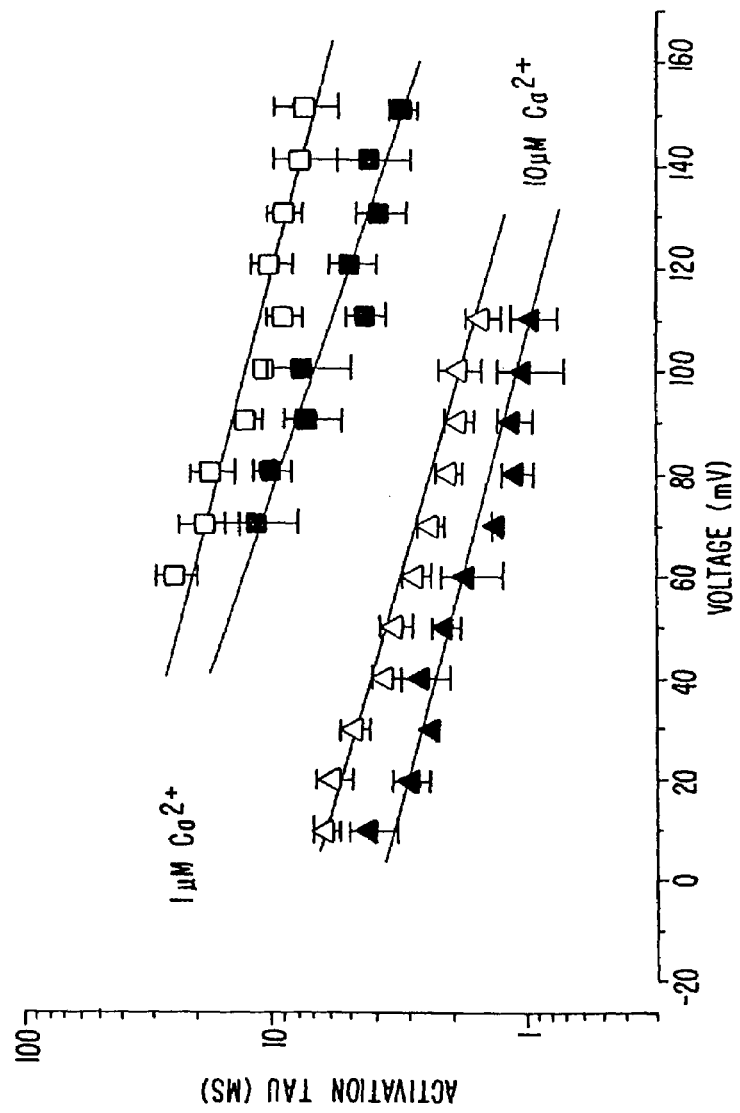
FIG. 5C.

US 6,994,968 B1

BK BETA SUBUNITS OF SLO FAMILY POTASSIUM CHANNELS

CROSS REFERENCE TO RELATED APPLICATIONS

This application is the national phase under 35 U.S.C. §371 of PCT/US00/04441, which was filed Feb. 22, 2000, and claims priority to U.S. Ser. No. 60/121,224, filed Feb. 23, 1999, and U.S. Ser. No. 60/163,367, filed Nov. 3, 1999, herein both incorporated by reference in their entirety.

FEDERALLY SPONSORED RESEARCH OR DEVELOPMENT

Not applicable.

FIELD OF THE INVENTION

The invention provides isolated nucleic acid and amino acid sequences of BK beta subunits 2, 3, and 4, which are auxiliary subunits of Slo potassium channels, antibodies to BK beta subunits 2–4, methods of detecting BK beta subunits 24, methods of screening for modulators of Slo potassium channels comprising BK beta subunits 2, 3, or 4, and kits for screening for modulators of Slo family potassium channels comprising BK beta subunits 2, 3, or 4.

BACKGROUND OF THE INVENTION

Potassium channels are involved in a number of physiological processes, including regulation of heartbeat, dilation of arteries, release of insulin, excitability of nerve cells, and regulation of renal electrolyte transport. Potassium channels are thus found in a wide variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are made by alpha subunits that fall into 8 families, based on predicted structural and functional similarities (Wei et al., *Neuropharmacology* 35(7):805–829 (1997)). Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25): 14066–71 (1997)) and are gated by both voltage and calcium or pH (Schreiber et al., *J. Biol. Chem.* 273:3509–16 (1998)). Another family, the inward rectifier potassium channels (Kir), belong to a structural family containing 2 transmembrane domains, and an eighth functionally diverse family (TP, or "two-pore") contains 2 tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493:625–633 (1996); Shi et al., *Neuron* 16(4):843–852 (1996)). In another example, the KQT family beta subunit, minK, primarily changes activation kinetics (Sanguinetti et al., *Nature* 384: 80–83 (1996)).

Slo or BK potassium channels are large conductance potassium channels found in a wide variety of tissues, both in the central nervous system and periphery. They play a key role in the regulation of processes such as neuronal integration, muscular contraction and hormone secretion. They may also be involved in processes such as lymphocyte differentiation and cell proliferation, spermatocyte differentiation and sperm motility. Three alpha subunits of the Slo family have been cloned, i.e., Slo1, Slo2, and Slo3 (Butler et al., *Science* 261:221–224 (1993); Schreiber et al., *J. Biol. Chem.*, 273:3509–16 (1998); and Joiner et al., *Nature Neurosci.* 1:462–469 (1998)). These Slo family members have been shown to be voltage and/or calcium gated, and/or regulated by intracellular pH.

A BK (or Slo) beta subunit that associates with Slo/BK potassium channels has been cloned and called BK beta 1 (Dworetzky et al., *J. Neurosci.* 16:4543–50 (1996); U.S. Pat. No. 5,776,734; see also Xia et al., *J. Neurosci.* 19:5255–5264 (1999), Wallner et al., *Proc. Nat'l Acad. Sci. USA* 96:4137–4142 (1999), Ali Riazi et al., *Genomics* 62:90–94 (1999), and EP 0 936 271 A1). BK beta 1 has short cytoplasmic N and C termini and has two membrane-spanning regions with a large extracellular loop. Functionally, BK beta 1 modulates the activation kinetics and calcium sensitivity of Slo1 channels (McManus et al., *Neuron* 14:645–50 (1995)). BK beta 1 also increases calcium sensitivity, sensitivity to extracellular toxins, and decreases the activation rate for Slo1 channels.

Additional beta subunits for Slo family potassium channels remain to be identified. The discovery and characterization of those Slo or BK beta subunits will provide important insights into how Slo potassium channels function in different environments, and how they respond to various activation mechanisms. Such information would also allow the identification of modulators of Slo potassium channels and the use of such modulators as therapeutic agents.

SUMMARY OF THE INVENTION

The present invention thus identifies for the first time BK beta 2, BK beta 3, and BK beta 4, each of which is a beta subunit of a Slo family potassium channel. These BK beta subunits have neither been previously cloned nor identified, and the present invention provides both the amino acid and nucleotide sequences of BK beta 2, BK beta 3, and BK beta 4.

In one aspect, the present invention provides an isolated nucleic acid encoding a beta subunit of a potassium channel, wherein the beta subunit: (i) forms, with at least one alpha unit, a Slo potassium channel; (ii) comprises an amino acid sequence that has greater than about 70% identity to the S1–S2 region of BK beta 2, BK beta 3, or BK beta 4; and (iii) specifically binds to polyclonal antibodies generated against SEQ ID NO:1, SEQ ID NO: 3, or SEQ ID NO:5.

In one aspect, the present invention provides an isolated nucleic acid encoding a beta subunit of a potassium channel, wherein the beta subunit: (i) forms, with at least one alpha subunit, a Slo potassium channel; (ii) comprises an amino acid sequence that has greater than about 70% identity to the S1–S2 region of BK beta 2, BK beta 3, or BK beta 4; and (iii) specifically binds to polyclonal antibodies generated against SEQ ID NO:1, SEQ ID NO:3, or SEQ ID NO:5; wherein said nucleic acid either: (i) selectively hybridizes under moderately stringent hybridization conditions to a nucleotide sequence of SEQ ID NO:2, SEQ ID NO:4, or SEQ ID NO:6; or (ii) encodes a protein which could be encoded by a nucleic acid that selectively hybridizes under moderately stringent hybridization conditions to a nucleotide of SEQ ID NO:2, SEQ ID NO:4, or SEQ ID NO:6.

In one embodiment, the nucleic acid is amplified by primers that selectively hybridize under stringent hybridization conditions to the same sequence as primers selected from the group consisting of:

| | |
|---|---|
| 5-ATGACAGCCTTTCCTGCCTCAGGGAAG-3 | (SEQ ID NO:7) |
| 5-AGATTTCTCTGCTCTTCCTTTGCTCCTCC-3 | (SEQ ID NO:8) |
| 5-GGCTGGCTGGACTGTAGAAGCATG-3 | (SEQ ID NO:9) |
| 5-GAGGCTGTCCAGATAAATCCCAAGTGC-3 | (SEQ ID NO:10) |
| 5-GGACTGAGAAGCCCATCATGGCAAACC-3 | (SEQ ID NO:11); |
| 5-ATGGCGAAGCTCCGGGTGGCTTAC-3 | (SEQ ID NO:12) |
| 5-TTAAGAGAACTTGCGCTTCTTCATGG-3 | (SEQ ID NO:13) |
| 5-GATGTGCTTCTGCATCGCACTCATG-3 | (SEQ ID NO:14); and |
| 5-AAGATGTCGATATGGACCAGTGGCC-3 | (SEQ ID NO:15) |
| 5-TTATCTATTGATCCGTTGGATCCTCTC-3 | (SEQ ID NO:16) |
| 5-CTCCTTCAGCTGTCCTCCAGACTGC-3 | (SEQ ID NO:17) |
| 5-GTCCCAGTAGAATAGCTCGGTCCTC-3 | (SEQ ID NO:18). |

In one embodiment, the nucleic acid encodes a beta subunit having a molecular weight of about between 24–34 kDa, 18–28 kDa, or 22–32 kDa. In another embodiment, the nucleic acid encodes human BK beta 2, 3, or 4. In another embodiment, the nucleic acid encodes SEQ ID NO:1, SEQ ID NO:3, or SEQ ID NO:5. In another embodiment, the nucleic acid has a nucleotide sequence of SEQ ID NO:2, SEQ ID NO:4, or SEQ ID NO:6.

In another aspect, the present invention provides an isolated beta subunit of a potassium channel, wherein the beta subunit: (i) forms, with at least one alpha subunit, a Slo potassium channel; (ii) comprises an amino acid sequence that has greater than about 70% identity to the S1–S2 region of BK beta 2, BK beta 3, or BK beta 4; and (iii) specifically binds to polyclonal antibodies generated against SEQ ID NO:1, SEQ ID NO:3, or SEQ ID NO:5.

In one embodiment, the beta subunit is human BK beta 2, 3, or 4. In another embodiment, the beta subunit has the sequence of SEQ ID NO:1, SEQ ID NO:3, or SEQ ID NO:5.

In another aspect, the present invention provides an antibody that selectively binds to a beta subunit as described above.

In another aspect, the present invention provides an expression vector comprising a nucleic acid as described above.

In another aspect, the present invention provides host cell transfected with an expression vector as described above.

In another aspect, the present invention provides a method for identifying a compound that increases or decreases ion flux through a potassium channel, the method comprising the steps of: (i) contacting the compound with a eukaryotic host cell or cell membrane in which has been expressed potassium channel comprising a beta subunit, wherein the beta subunit: (a) forms, with at least one alpha subunit, a Slo potassium channel; (b) comprises an amino acid sequence that has greater than about 70% identity to the S1–S2 region of a BK beta 2, BK beta 3, or a BK beta 4; and (c) specifically binds to polyclonal antibodies generated against SEQ ID NO:1, SEQ ID NO:3, or SEQ ID NO:5; and (ii) determining the functional effect of the compound upon the cell or cell membrane expressing the Slo potassium channel.

In one embodiment, the functional effect is determined by measuring changes in current or voltage. In another embodiment, the beta subunit is recombinant. In one embodiment, the beta subunit is human BK beta 2, 3, or 4. In another embodiment, the beta subunit has the sequence of SEQ ID NO:1, SEQ ID NO:3, or SEQ ID NO:5.

In another aspect, the present invention provides a method of detecting the presence of BK beta 2, 3 or 4 in a sample, the method comprising the steps of: (i) isolating a biological sample; (ii) contacting the biological sample with a BK beta 2, 3, or 4-specific reagent that selectively associates with BK beta 2, 3, or 4; and, (iii) detecting the level of BK beta 2, 3, or 4-specific reagent that selectively associates with the sample.

In one embodiment, the BK beta specific reagent is selected from the group consisting of: BK beta specific antibodies, BK beta specific oligonucleotide primers, and BK beta specific-nucleic acid probes. In another embodiment, the sample is from a human.

In another aspect, the present invention provides, in a computer system, a method of screening for mutations of human BK beta 2, BK beta 3, or BK beta 4 genes, the method comprising the steps of: (i) entering into the system at least about 25 nucleotides of first nucleic acid sequence encoding a beta subunit having a nucleotide sequence of SEQ ID NO:2, SEQ ID NO:4, or SEQ ID NO:6; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state.

In aspect, the present invention provides a computer readable substrate comprising the first nucleic acid sequence.

In another aspect, the present invention provides, in a computer system, a method for identifying a three-dimensional structure of BK beta 2, BK beta 3, or BK beta 4 subunits, the method comprising the steps of: (i) entering into the system an amino acid sequence of at least 25 amino acids of a beta subunit or at least 75 nucleotides of a gene encoding the beta subunit, the beta subunit having an amino acid sequence of SEQ ID NO:1, SEQ ID NO:3, or SEQ ID NO:5; and (ii) generating a three-dimensional structure of the beta subunit encoded by the amino acid sequence.

In another aspect, the present invention provides a computer readable substrate comprising the three dimensional structure of the beta subunit.

In one embodiment, the amino acid sequence is a primary structure and wherein said generating step includes the steps of: (i) forming a secondary structure from said primary structure using energy terms determined by the primary structure; and (ii) forming a tertiary structure from said secondary structure using energy terms determined by said secondary structure. In another embodiment, said generating step further includes the step of forming a quaternary structure from said tertiary structure using anisotropic terms encoded by the tertiary structure. In another embodiment, the method further comprises the step of identifying regions of the three-dimensional structure of a BK beta 2, BK beta 3 or BK beta 4 subunit that bind to ligands and using the regions to identify ligands that bind to the beta subunit.

BRIEF DESCRIPTION OF THE DRAWINGS

FIG. 1: Alignment of the deduced amino acid sequence of human BK beta 1, 2, 3, and 4. Residues conserved in three or more proteins are shaded. Gaps in the alignment are indicated by dashes. Amino acid numbers are given at the left margin. Two predicted transmembrane domains are outlined in black. The Genbank accession number for the BK beta 1 sequence is U38907 (Dworetsky et al., *J. Neurosci.* 16:4543–4550 (1996).

FIG. 5. Effect of BK beta 3 on the time-course of Slo-1 activation. Voltage clamp records show Slo-1 current activation, in the absence (A) or presence (B) of BK beta 3, following a series of 500 ms depolarizing steps (–100 mV to +150 mV in 10 mV increments) from a holding potential of –140 mV. Free Ca2+ was 10 $\mu$M, scale bars represent 1 nA and 10 ms. Currents elicited by depolarizing voltage steps were fit with a single exponential function. Activation rates ($\tau$ act, ms) were determined in intracellular solutions containing either 1 $\mu$M (squares) or 10 $\mu$M (triangles) free Ca2+, in the absence (solid symbols) or presence (open symbols) of BK beta 3. BK beta 3 produced a slowing of activation at all voltages in the presence of 1 $\mu$M and 10 $\mu$M free Ca2+. Symbols represent the mean of 8–12 experiments, vertical lines represent the S.E.M.

FIG. 6. Slo-1/BKB3 forms BK type II-like charybdotoxin-(CTX) insensitive channels. Slo-1 (A) or Slo-1+BK beta 3 (B) were expressed in HEK293 cells and membrane currents measured using the whole-cell voltage-clamp technique. Currents were elicited with 250 ms depolarizing steps (to –20 mV in the examples shown) from a holding potential of –80 mV.

DETAILED DESCRIPTION OF THE INVENTION

I. Introduction

Figure 2:
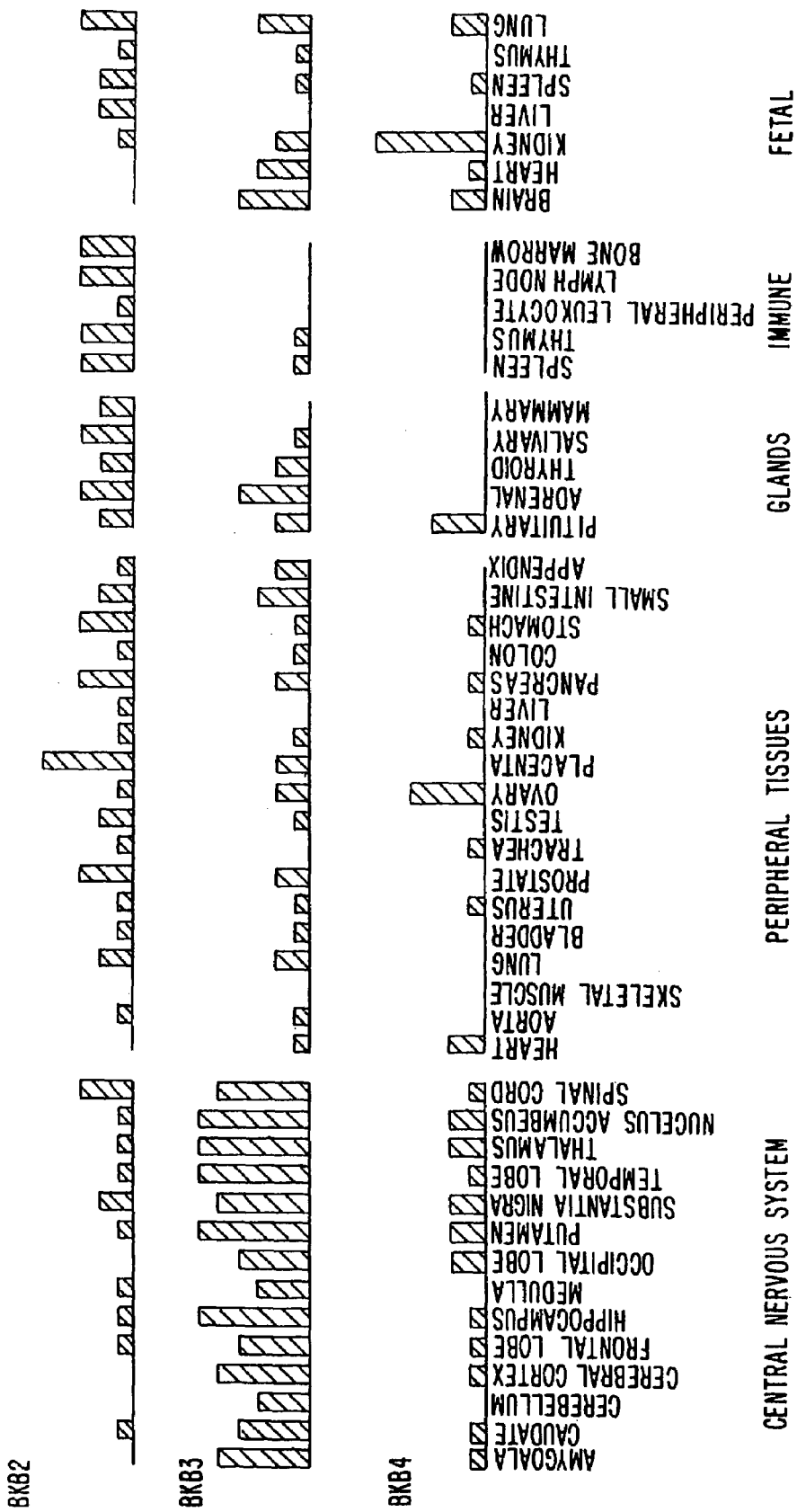
FIG. 2: Messenger RNA expression patterns for human BK beta 2, 3, and 4. Height of bars indicates expression level relative to the highest expression level seen for that gene. All data comes from hybridization of $^{32}$P-labeled cDNA probes against human mRNA masterblots (Clontech).

The present invention provides for the first time nucleic acids encoding novel potassium channel beta subunits BK beta 2, BK beta 3, and BK beta 4, identified and cloned from human tissues. These beta subunits are polypeptide monomers having two transmembrane domains separated by a large extracellular linker. BK beta subunits associate with alpha subunit monomers from the Slo gene family to produce Slo potassium channels. The larger Slo family alpha polypeptide monomers contain six or seven transmembrane domains that form the ion-conducting core of a Slo potassium channel, while the BK beta monomers regulate channel kinetics, expression levels, and sensitivity to bound ligands. Because Slo potassium channels can open at subthreshold voltages in the presence of sufficient intracellular calcium, they have significant roles in maintaining the resting potential and in controlling excitability of a cell. Altering the calcium sensitivity, kinetics, and expression levels of these Slo channels with BK beta subunits is likely to result in changes in firing frequency and secretion levels.

The invention also provides methods of screening for modulators of Slo potassium channels comprising a BK beta subunit 2, 3, or 4. Because of the importance of Slo channels to firing frequency and secretion, such modulators of Slo channel activity are useful for treating CNS disorders such as migraines, hearing and vision problems, learning and memory problems, learning and memory problems, seizures, psychotic disorders, and as neuroprotective agents (e.g., to prevent stroke). They are also useful in treating disorders of vascular and muscle tone, breathing (asthma), hormone secretion, spermatocyte differentiation and motility, lymphocyte differentiation and cell proliferation.

Furthermore, the invention provides assays for a Slo potassium channel activity, where the channel comprising BK beta subunit 2, 3, or 4 acts as a direct or indirect reporter molecule. Such uses of the Slo potassium channel as a reporter molecule in assay and detection systems have broad applications, e.g., the Slo potassium channel can be used as a reporter molecule to measure changes in potassium concentration, membrane potential, current flow, ion flux, transcription, signal transduction, receptor-ligand interactions, second messenger concentrations, in vitro, in vivo, and ex vivo. In one embodiment, the Slo potassium channel can be used as an indicator of current flow in a particular direction (e.g., outward or inward potassium flow), and in another embodiment, the Slo potassium channel can be used as an indirect reporter via attachment to a second reporter molecule such as green fluorescent protein.

Finally, the invention provides for methods of detecting BK beta subunits 2–4 nucleic acid and protein expression, allowing investigation of the channel diversity provided by the beta subunits and the regulation/modulation of channel activity provided by the beta subunits, as well as diagnosis of disease involving abnormal ion flux, including diagnosis of CNS disorders such as migraines, hearing and vision problems, learning and memory problems, seizures, and psychotic disorders, as well as disorders of vascular and muscle tone, breathing (asthma), hormone secretion, spermatocyte differentiation and motility, lymphocyte differentiation and cell proliferation.

Functionally, these BK beta subunits 2–4 are subunits of a Slo potassium channel. Such Slo potassium channels comprising the beta subunits may contain one or more beta subunits along with alpha subunits from the Slo family, e.g., Slo1, Slo2, or Slo3. The presence of the beta subunits in a Slo potassium channel modulates the activity of the channel and thus enhances channel diversity. For example, when a beta subunit associates with other alpha monomers, the resulting channel may have an altered single channel conductance as well as altered kinetic properties, e.g., changes in activation or inactivation rates. Beta subunits have been known to increase the number of channels by helping the alpha subunits get to the cell surface. BK beta subunits 2–4 also affect pharmacology, and change the sensitivity of the channel to natural ligands. For example, BK beta 3 increases the calcium sensitivity of Slo1 potassium channels and slowed activation kinetics, and BK beta 4 slows activation kinetics.

Structurally, each of the nucleotide sequences of BK beta subunits 2–4 (e.g., SEQ ID NO:2, SEQ ID NO:4, or SEQ ID NO:6) encodes a polypeptide monomer of a different size (SEQ ID NO:1, SEQ ID NO:3, or SEQ ID NO:5, respectively). The nucleotide sequence of BK beta 2 encodes a polypeptide monomer of approximately 257 amino acids with a predicted molecular weight of approximately 29 kDa (SEQ ID NO:1) and a predicted range of 24–34 kDa. The nucleotide sequence of BK beta 3 encodes a polypeptide monomer of approximately 210 amino acids with a predicted molecular weight of approximately 23 kDa (SEQ ID NO:3) and a predicted range of 18–28 kDa. The nucleotide sequence of BK beta 4 encodes a polypeptide monomer of approximately 235 amino acids with a predicted molecular weight of approximately 27 kDa (SEQ ID NO:5) and a predicted range of 22–32 kDa.

The present invention also provide polymorphic variants of BK beta subunits 2–4, as depicted in SEQ ID NO:1 for BK beta 2, SEQ ID NO:3 for BK beta 3, and SEQ ID NO:5 for BK beta 4, as follows.

For BK beta 2, in variant #1, a leucine residue is substituted for a valine residue at amino acid position 37; in variant #2, a leucine residue is substituted for an isoleucine residue at amino acid position 76; in variant #3, a valine residue is substituted for a isoleucine residue at amino acid position 152; in variant #4, a isoleucine residue is substituted for a leucine residue at amino acid position 217.

For BK beta 3, in variant #1, a methionine residue is substituted for a isoleucine residue at amino acid position 25; in variant #2, a leucine residue is substituted for a phenylalanine residue at amino acid position 35; in variant #3, a lysine residue is substituted for an arginine residue at amino acid position 97; in variant #4, a methionine residue is substituted for a isoleucine residue at amino acid position 168.

For BK beta 4, in variant #1, a valine residue is substituted for an isoleucine residue at amino acid position 59; in variant #2, an asparagine residue is substituted for a glutamine residue at amino acid position 83; in variant #3, a phenylalanine residue is substituted for a leucine residue at amino acid position 200; in variant #4, an isoleucine residue is substituted for a valine residue at amino acid position 214.

Specific regions of BK beta subunits 2–4 nucleotide and amino acid sequence may be used to identify polymorphic variants, interspecies homologs (orthologs), mutants, and alleles of BK beta subunits 2–4. This identification can be made in vitro, e.g., under stringent hybridization conditions and sequencing, or by using the sequence information in a computer system for comparison with other nucleotide sequences. Typically, identification of polymorphic variants and alleles of BK beta subunits is made by comparing the amino acid sequence of the S1–S2 region, which is comprised of the entire first two transmembrane domains, including the intervening extracellular domain. For BK beta 2, the S1–S2 region is approximately amino acids 39–209 (see, e.g., SEQ ID NO:1). For BK beta 3, the S1–S2 region is approximately amino acids 20–191 (see, e.g., SEQ ID NO:3). For BK beta 4, the S1–S2 region is approximately amino acids 50–217 (see, e.g., SEQ ID NO:5). Amino acid identity of about 70% or above, preferably 85%, more preferably 90–95% or above to either the S1–S2 region, or the entire BK beta subunit polypeptide, typically demonstrates that a protein is a polymorphic variant, interspecies homolog, or allele of a BK beta subunit. Sequence comparison can be performed using any of the sequence comparison algorithms discussed below. Antibodies that bind specifically to a BK beta subunit can also be used to identify alleles, interspecies homologs, and mutants polymorphic variants.

Polymorphic variants, interspecies homologs, and alleles of BK beta subunits 2–4 are confirmed by co-expressing the putative BK beta subunit with a Slo family alpha subunit, e.g., Slo1, Slo2, or Slo3, and examining whether the beta subunit associates with a Slo potassium channel when co-expressed with a member of the Slo family. Functional assays may be used to determine the characteristics of the Slo potassium channels formed in such ways. One assay is to determine changes in cellular polarization by measuring changes in current (thereby measuring changes in polarization) with voltage-clamp and patch-clamp techniques, e.g., "the cell-attached" mode, "the inside-out" mode, and "the whole cell" mode (see, e.g., Ackerman et al., *New Engl. J. Med.* 336:1575–1595 (1997)). These assays are used to demonstrate that a potassium channel comprising a beta subunit having about 70% or greater, preferably 90% or greater amino acid identity to the S1–S2 region, or the entire sequence of a BK beta subunit such as BK beta 2, BK beta 3, or BK beta 4, is a species of a BK beta subunit 2, 3, or 4 because the subunit shares the same functional characteristics. Typically, BK beta subunits having the amino acid sequence of SEQ ID NO:1, SEQ ID NO:3, or SEQ ID NO:5, are used as positive controls in comparison to the putative the BK beta subunit protein to demonstrate the identification of a polymorphic variant or allele of a BK beta subunit.

BK beta subunit 2–4 nucleotide and amino acid sequence information may also be used to construct models of a Slo potassium channel in a computer system. These models are subsequently used to identify compounds that can activate or inhibit Slo potassium channels comprising BK beta subunits 2, 3, or 4. Such compounds that modulate the activity of channels comprising BK beta subunits 2, 3, or 4 can be used to investigate the role of the BK beta subunits in modulation of channel activity and in channel diversity.

The identification and cloning of BK beta subunits 2–4 for the first time provides a means for assaying for inhibitors and activators of Slo potassium channels that comprise BK beta subunits 2, 3, or 4. Biologically active BK beta subunits 2–4 are useful for testing inhibitors and activators of Slo potassium channels comprising a BK beta subunit and other Slo family members using in vivo and in vitro expression that measure, e.g., changes in voltage or current. Such activators and inhibitors identified using a Slo potassium channel comprising at least one BK beta subunit can be used to further study, e.g., regulation of the Slo family potassium channel, channel kinetics and conductance properties of channels. Such activators and inhibitors are also useful as pharmaceutical agents for treating disease involving abnormal ion flux, including diagnosis of CNS disorders such as migraines, hearing and vision problems, learning and memory problems, seizures, and psychotic disorders, as well as disorders of vascular and muscle tone, breathing (asthma), hormone secretion, spermatocyte differentiation and motility, lymphocyte differentiation and cell proliferation.

Methods of detecting BK beta subunits 2–4 and expression of channels comprising a BK beta subunit are also useful for diagnostic applications for diseases involving abnormal ion flux, e.g., CNS disorders and other disorders described above. For example, chromosome localization of the gene encoding BK beta subunits 2–4 can be used to identify diseases caused by and associated with the BK beta subunits. Methods of detecting BK beta subunits 2–4 are also useful for examining the role of BK beta subunits in Slo potassium channel diversity and modulation of Slo potassium channel activity.

II. Definitions

As used herein, the following terms have the meanings ascribed to them unless specified otherwise.

The term "Slo family potassium channels" refers to a group of potassium channels composed of alpha subunits having a core ion channel motif of 6 or 7 transmembrane domains and a pore domain (Butler et al., *Science* 261: 221–224 (1993); Meera et al., *Proc. Natl. Acad. Sci. U.S.A.* 94:14066–71 (1997); Schreiber et al., *J. Biol. Chem.* 273: 3509–16 (1998); Joiner et al., *Nature Neurosci.* 1:462–469 (1998)), and a long C-terminal domain that appears to be involved in channel gating (Wei et al., *Neuron* 13:671–681 (1994)). At least 3 members of this gene family exist in mammals: Slo1 (Butler et al., *Science* 261: 221–224 (1993); McCobb et al., *Am. J. Physiol.* 269:H767–H777 (1995)), Slo2 (Joiner et al., *Nature Neurosci.* 1:462–469 (1998)) and Slo3 (Schreiber et al., *J. Biol. Chem.* 273:3509–16 (1998)). The Slo family channels have relatively large conductance, ranging from 40–65 pS for Slo2 up to almost 300 pS for Slo1. Each Slo family channel is dually gated by voltage and a second stimulus. For Slo1 and Slo2 that second stimulus is intracellular calcium, and for Slo3 it is intracellular pH. The Slo family channels can be identified on the basis of amino acid homology in a region extending from the pore domain into the C-terminus, corresponding to amino acids 273–494 of the mouse Slo3 sequence (Schreiber et al., *J. Biol. Chem.* 273:3509–16 (1998)). In this region, each Slo family member shares at least 25% amino acid identity to other Slo family members in pairwise comparisons. Slo1 and Slo3 share more than 50% identity over this region, whereas Slo2 is between 25–30% identical. No other channels share this level of identity with Slo channels over the entire length of this region (see FIG. 1).

Figures 6A, 6B:
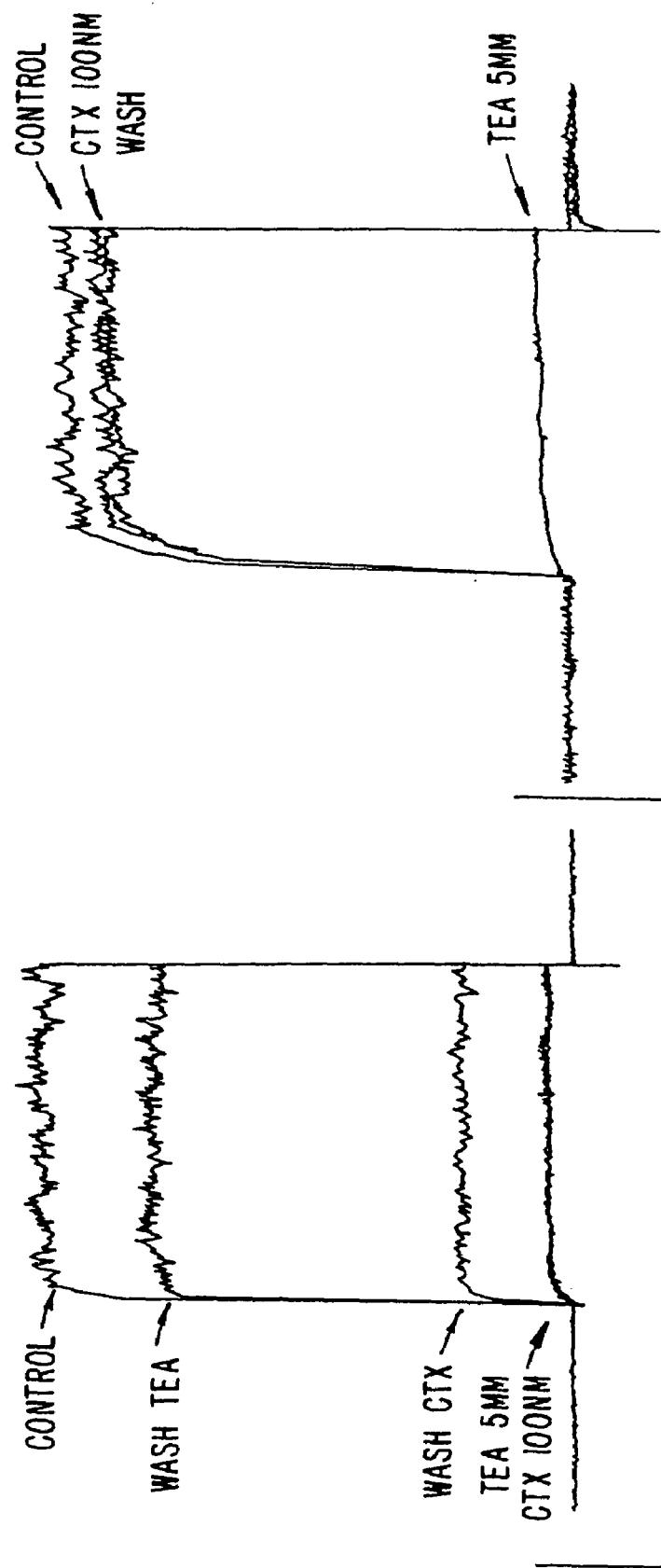
As illustrated in FIG. 6A, membrane currents in cells expressing Slo-1 alone were strongly inhibited by both TEA (5 mM) and CTX (100 nM). In contrast, membrane currents in cells co-expressing Slo-1 and BK beta 3 were TEA (5 mM) sensitive but CTX (100 nM) insensitive (FIG. 6B). Similar recordings were made from 4 cells expressing Slo-1 alone and 6 cells co-expressing Slo-1/BKB3. Scale bars represent 1 nA and 200 ms.

The phrase "type II BK potassium channel" refers to a BK or Slo channel that has slowed activation kinetics and resistance to charybdotoxin block, e.g., Slo1/BK Beta 3 (see, e.g., Reinhart et al., *Neuron* 2:1031–1041 (1989); see also FIG. 6).

The term "beta subunits" refers to polypeptide monomers that are auxiliary subunits of a potassium channel composed of alpha subunits; however, beta subunits alone cannot form a channel (see, e.g., U.S. Pat. No. 5,776,734). Beta subunits function, for example, to increase the number of channels by helping the alpha subunits reach the cell surface, change activation kinetics, and change the sensitivity of natural ligands binding to the channels. For example, BK beta 3 increases the calcium sensitivity of Slo1 potassium channels and slowed activation kinetics, and BK beta 4 slows activation kinetics. The beta subunits can be outside of the pore region and associated with alpha subunits comprising the pore region. They can also contribute to the external mouth of the pore region.

The term "transmembrane domain" refers to the region of the potassium channel subunit polypeptide that spans across the lipid bilayer membrane of the cells. Various families of the potassium channels have different numbers of transmembrane domains that travel across the cellular membrane. Structurally, a transmembrane domain starts from the first amino acid residue of the subunit sequence that enters into the cellular membrane and ends with the last amino acid residue in the subunit sequence that leaves the cellular membrane.

"Homomeric" refers to a potassium channel composed of identical alpha subunits, while "heteromeric" refers to a potassium channel composed of two or more different types of alpha subunits. Both heteromeric and homomeric channels can also include auxiliary beta subunits such as the BK beta subunits of the present invention.

The phrase "S1–S2 region" refers to the region of a BK beta subunit 2–4 polypeptide comprising the entire first two transmembrane domains, including the intervening extracellular domain (approximately amino acids 39–209 of BK beta 2, see SEQ ID NO:1; or amino acids 20–191 of BK beta 3 see SEQ ID NO:3; or amino acids 50–217 of BK beta 4, see SEQ ID NO:5). This region is defined as the fragment from the first residue of the first transmembrane domain to the last residue of the second transmembrane domain. This region can be used to identify the polymorphic variants, interspecies homologs, mutants, and alleles of BK beta subunits.

The term "BK beta subunit" refers to a beta subunit of "BK" (large conductance) potassium channel, also known as "Slo potassium channels." The term "BK beta subunits 2–4" refers to BK beta 2, BK beta 3, and/or BK beta 4. A BK beta subunit is a polypeptide that is an auxiliary subunit or monomer of a Slo family potassium channel. When a BK beta subunit is part of a Slo potassium channel, the channel has the characteristics of a Slo family channel, e.g., it is dually gated by voltage and a second stimulus such as calcium or pH. BK beta subunits therefore refer to polymorphic variants, alleles, mutants, and interspecies homologs that: (1) have an S1–S2 or a full length coding region that has greater than about 70% amino acid sequence identity, preferably about 80–90% amino acid sequence identity to S1–S2 or a full length sequence of SEQ ID NO:1, SEQ ID NO:3, or SEQ ID NO:5; (2) bind to polyclonal antibodies raised against an immunogen comprising an amino acid sequence selected from the group consisting of SEQ ID NO:1, SEQ ID NO:3, or SEQ ID NO:5, and conservatively modified variants thereof; (3) specifically hybridize under stringent hybridization conditions to a sequence selected from the group consisting of SEQ ID NO:2, SEQ ID NO:4, or SEQ ID NO:6, and conservatively modified variants thereof; or (4) are amplified by primers that specifically hybridize under stringent hybridization conditions to the same sequence as a primers selected from the group consisting of SEQ ID NO:7, SEQ ID NO:8, SEQ ID NO:9, SEQ ID NO:10, and SEQ ID NO:1 (BK beta 2); or SEQ ID NO:12, SEQ ID NO:13 and SEQ ID NO:14 (BK beta 3); or SEQ ID NO:15, SEQ ID NO:16, SEQ ID NO:17 and SEQ ID NO:18 (BK beta 4).

The phrase "functional effects" in the context of assays for testing compounds that modulate Slo channels comprising BK beta subunits includes the determination of any parameter that is indirectly or directly under the influence of the Slo channel comprising a BK beta subunit. It includes changes in ion flux, membrane potential, current flow, transcription, ligand binding, G-protein binding, phosphorylation or dephosphorylation, signal transduction, receptor-ligand interactions, second messenger concentrations (e.g., cAMP, $IP_3$, or intracellular $Ca^{2+}$), as measured in vitro, in vivo, and ex vivo, and also includes other physiologic effects such increases or decreases of neurotransmitter or hormone release.

By "determining the functional effect" is meant assays for a compound that increases or decreases a parameter that is indirectly or directly under the influence of BK beta subunit 2, 3, or 4. Such functional effects, e.g., physical and chemical effects, can be measured by any means known to those skilled in the art, e.g., patch clamping, voltage-sensitive dyes, whole cell currents, radioisotope efflux, inducible markers, oocyte or tissue culture cell expression of BK beta subunits; transcriptional activation; ligand binding assays; voltage, membrane potential and conductance changes; ion flux assays; ligand binding, hanges in intracellular second messengers such as cAMP and inositol triphosphate ($IP_3$); changes in intracellular calcium levels; neurotransmitter release, and the like.

"Inhibitors," "activators," and "modulators" of the Slo potassium channels comprising BK beta subunits 2, 3, or 4 refer to modulator molecules identified using in vitro and in vivo assays for channel function. Inhibitors are compounds that decrease, block, prevent, delay activation, inactivate, desensitize, or down regulate the channel. Activators are compounds that increase, open, activate, facilitate, enhance activation, sensitize or up regulate channel activity. Modulators include naturally occurring and synthetic ligands, antagonists, agonists, small chemical molecules and the like. Assays for inhibitors and activators include, e.g., co-expressing a BK beta subunit with an alpha subunit in cells or cell membranes, applying putative modulator compounds, and then measuring flux of ions through the Slo channel and determining the functional effect of the modulator as described above.

Samples or assays comprising a Slo potassium channel comprising BK beta 2, 3, or 4 that are treated with a potential activator or inhibitor are compared to control samples without the inhibitor, to examine the extent of inhibition. Control samples (Slo channels comprising a BK beta subunit, untreated with inhibitors) are assigned a relative Slo potassium channel activity value of 100%. Inhibition of channels comprising a BK beta subunit is achieved when the Slo potassium channel activity value relative to the control is about 90%, preferably 50%, more preferably 25–0%. Activation of Slo channels comprising BK beta subunits is achieved when the Slo potassium channel activity value relative to the control is 110%, more preferably 150%, more preferably 200–500% or 1000% and higher.

"Biologically active" BK beta subunit refers to BK beta subunits that are part of a potassium channel having Slo family channel activity, tested as described above. Typically, such potassium channel contains at least one type of alpha subunit, optionally more than one type of alpha subunit, and one or more BK beta subunits. Typically the potassium channels comprises at least one or two, preferably four alpha subunits, either identical or different.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid encoding a BK beta subunit is separated from open reading frames that flank the BK beta subunit gene and encode proteins other than a BK beta subunit. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an carbon that is bound to a hydrogen, a carboxyl group, an amino group, and an R group., e.g., homoserine, norleucine, methionine sulfoxide, and methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes (A, T, G, C, U, etc.).

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).

(see, e.g., Creighton, Proteins (1984) for a discussion of amino acid properties).

A "label" is a composition detectable by spectroscopic, photochemical, biochemical, immunochemical, or chemical means. For example, useful labels include 32P, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:1 can be made detectable, e.g., by incorporating a radiolabel into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides (i.e., 70%, 75%, 80%, 85%, 90%, or 95% identity) that are the same, when compared and aligned for maximum correspondence over a comparison window, as measured using one of the following sequence comparison algorithms with the default parameters listed below, or by manual alignment and visual inspection. Such sequences are then said to be "substantially identical." This definition also refers to the complement of a test sequence. Preferably, the percent identity exists over a region of the sequence that is at least about 25 amino acids in length, more preferably over a region that is 50 or 100 amino acids in length.

For sequence comparison, one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387–395 (1984).

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleotide sequences are substantially identical is that the same primers can be used to amplify both sequences.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially an Fab with part of the hinge region (see Fundamental Immunology (Paul ed., 3$^{rd}$ ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552–554 (1990); Marks et al., *Biotechnology* 10:779–783 (1992)).

An "anti-BK beta subunit antibody" is an antibody or antibody fragment that specifically binds a polypeptide encoded by a BK beta subunit gene, cDNA, or a subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a BK beta subunit with the amino acid sequence of the subunit association region encoded in SEQ ID NO:1 can be selected to obtain only those polyclonal antibodies that are specifically immunoreactive with the S1–S2 region of BK beta subunit 2 and not with other proteins, except for polymorphic variants and alleles of BK beta subunits. This selection may be achieved by subtracting out antibodies that cross react with molecules such as other BK beta subunits. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "host cell" is meant that a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that contains a BK beta subunit or nucleic acid encoding a BK beta subunit protein. Such samples include, but are not limited to, tissue isolated from humans. Biological samples may also include sections of tissues such as frozen sections taken for histological purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

III. Isolation of the Genes Encoding BK Beta Subunits

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding BK Beta Subunits In general, the nucleic acid sequences encoding a beta subunit such as BK beta 2, BK beta 3, and BK beta 4, and related nucleic acid sequence homologs are cloned from cDNA and genomic DNA libraries or isolated using amplification techniques with oligonucleotide primers. For example, BK beta 2 sequences are typically isolated from mouse or human nucleic acid (genomic or cDNA) by hybridizing with a nucleic acid probe or primer, the sequence of which can be derived from SEQ ID NO:2, preferably from the S1–S2 region of BK beta 2. Likewise, BK beta 3 sequences are typically isolated from mouse or human nucleic acid (genomic or cDNA) by hybridizing with a nucleic acid probe or primer, the sequence of which can be derived from SEQ ID NO:4, preferably from the S1–S2 region of BK beta 3. BK beta 4 sequences are typically isolated from mouse or human nucleic acid (genomic or cDNA) by hybridizing with a nucleic acid probe or primer, the sequence of which can be derived from SEQ ID NO:6, preferably from the S1–S2 region of BK beta 4.

Suitable tissues from which RNA and cDNA encoding BK beta subunits can be isolated are as follows. For BK beta 2, the tissues include testis, B cells, fetal heart, pregnant uterus, and melanocytes. BK beta 3 is highly expressed in the brain. See Example II for a complete list of the tissues where BK beta 3 is expressed. For BK beta 4, heart and fetal kidney tissue are among the tissues from which it can be isolated. See Example III for a complete list of the tissues where BK beta 4 is expressed.

Amplification techniques using primers can also be used to amplify and isolate BK beta subunits 2–4 from DNA or RNA. The following primers can be used to amplify a sequence of BK beta 2, BK beta 3, or BK beta 4:

The following primers can be used to amplify a sequence of BK beta 2:

| | |
|---|---|
| 5-ATGACAGCCTTTCCTGCCTCAGGGAAG-3 | (SEQ ID NO:7) |
| 5-AGATTTCTCTGCTCTTCCTTTGCTCCTCC-3 | (SEQ ID NO:8) |
| 5-GGCTGGCTGGACTGTAGAAGCATG-3 | (SEQ ID NO:9) |
| 5-GAGGCTGTCCAGATAAATCCCAAGTGC-3 | (SEQ ID NO:10) |
| 5-GGACTGAGAAGCCCATCATGGCAAACC-3 | (SEQ ID NO:11). |

Primers 7 and 8 can be used to amplify the entire coding region. Primers 7 and 9 can be used to amplify the 5' half, while primers 8 and 10 can be used to amplify the 3' half Primers 7 and 11 or 9 and 10 can be used to amplify splice variants, as each set is in the same exon.

The following primers can be used to amplify a sequence of BK beta 3:

| | |
|---|---|
| 5-ATGGCGAAGCTCCGGGTGGCTTAC-3 | (SEQ ID NO:12) |
| 5-TTAAGAGAACTTGCGCTTCTTCATGG-3 | (SEQ ID NO:13) |
| 5-GATGTGCTTCTGCATCGCACTCATG-3 | (SEQ ID NO:14). |

Primers 12 and 13 can be used to amplify the entire coding region and primers 13 and 14 can be used to amplify splice variants, as they are in the same exon.

The following primers can be used to amplify a sequence of BK beta 4:

| | |
|---|---|
| 5-AAGATGTCGATATGGACCAGTGGCC-3 | (SEQ ID NO:15) |
| 5-TTATCTATTGATCCGTTGGATCCTCTC-3 | (SEQ ID NO:16) |
| 5-CTCCTTCAGCTGTCCTCCAGACTGC-3 | (SEQ ID NO:17) |
| 5-GTCCCAGTAGAATAGCTCGGTCCTC-3 | (SEQ ID NO:18). |

Primers 15 and 16 can be used to amplify the entire coding region. Primers 15 and 18 can be used to amplify the 5' half, and primers 16 and 17 can be used to amplify the 3' half.

These primers can be used, e.g., to amplify either the full length sequence or a probe of one to several hundred nucleotides, which is then used to screen a human or mouse library for full-length BK beta subunit genes.

Nucleic acids encoding BK beta subunits 2–4 can also be isolated from expression libraries using antibodies as probes. Such polyclonal or monoclonal antibodies can be raised using the sequence of SEQ ID NO:1 (for BK beta 2), SEQ ID NO:3 (for BK beta 3), and SEQ ID NO:5 (for BK beta 4); or raised using the S1–S2 region of a BK beta subunit.

For BK beta subunits 2–4, polymorphic variants, alleles, and interspecies homologs that are substantially identical to a BK beta subunit can be isolated using BK beta subunit nucleic acid probes and oligonucleotides under stringent hybridization conditions, by screening libraries. Alternatively, expression libraries can be used to clone each of the BK beta subunits 2–4 and their polymorphic variants, alleles, and interspecies homologs, by detecting expressed homologs immunologically with antisera or purified antibodies made against the S1–S2 region of BK beta subunits 2–4, which also recognize and selectively bind to the homolog.

To make a cDNA library, one should choose a source that is rich in mRNA of the particular BK beta subunit. For example, for BK beta 2, a cDNA library from placenta, testis, or B cells is used. For BK beta 3, a cDNA library from hippocampus is used. For BK beta 4, a cDNA library from heart is used. For a more extensive list of tissues in which these subunits are expressed, see FIG. 2 and Example I. In each case, the mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA, preferably mouse or human, is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. U.S.A.,* 72:3961–3965 (1975).

An alternative method of isolating the nucleic acid and the homologs of BK beta subunits 2–4 combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of a BK beta subunit directly from mRNA, from cDNA, from genomic libraries or cDNA libraries. Degenerate oligonucleotides can be designed to amplify a BK beta subunit homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of mRNA encoding a BK beta subunit in physiological samples, for nucleic acid sequencing, or for other purposes. Genes amplified by the PCR reaction can be purified from agarose gels and cloned into an appropriate vector.

Gene expression of BK beta subunits 2–4 can also be analyzed by techniques known in the art, e.g., reverse transcription and amplification of mRNA, isolation of total RNA or poly A+ RNA, northern blotting, dot blotting, in situ hybridization, RNase protection, probing high density oligonucleotide arrays, and the like.

Synthetic oligonucleotides can be used to construct recombinant genes of BK beta subunits 2–4 for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of a BK beta subunit gene. The specific subsequence is then ligated into an expression vector.

The genes for BK beta subunits 2–4 are typically cloned into intermediate vectors before transformation into prokaryotic or eukaryotic cells for replication and/or expression. These intermediate vectors are typically prokaryote vectors, e.g., plasmids, or shuttle vectors.

C. Expression of BK Beta Subunits 2–4 in Prokaryotes and Eukaryotes

To obtain high level expression of a cloned gene, such as those cDNAs encoding BK beta subunits 2–4, one typically subclones a BK beta subunit gene into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing a BK beta subunit protein are available in, e.g., *E. col*, Bacillus sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of nucleic acid encoding a BK beta subunit in host cells. A typical expression cassette thus contains a promoter operably linked to the nucleic acid sequence encoding a BK beta subunit and signals required for efficient polyadenylation of the transcript, ribosome binding sites, and translation termination. The nucleic acid sequence encoding BK beta subunit may be linked to a cleavable signal peptide sequence to promote secretion of the encoded protein by the transformed cell, for isolation of individual subunits, e.g., for production of antibodies. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette can also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification, using genes such as such as thymidine kinase and dihydrofolate reductase. Alternatively, high yield expression systems not involving gene amplification are also suitable, such as using a baculovirus vector in insect cells, with sequence encoding BK beta subunits 2, 3, or 4 under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of a BK beta subunit, which is then purified using standard techniques (see, e.g., Colley et al., *J. Biol. Chem.* 264:17619–17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing a BK beta subunit.

After the expression vector is introduced into the cells, the transfected cells are cultured under conditions favoring expression of the BK beta subunit, which is recovered from the culture using standard techniques identified below.

IV. Purification of BK Beta Subunits 2–4

Either naturally occurring or recombinant BK beta subunits 2–4 can be purified for use in functional assays to identify modulators of Slo channels comprising BK beta subunits. Naturally occurring BK beta subunits 2–4 can be purified, e.g., from mouse or human tissue such as testis, heart, or hippocampus tissue and any other source of a BK beta subunit. Recombinant BK beta subunits 2–4 are purified from any suitable expression system.

BK beta subunits 2–4 may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when a recombinant BK beta subunit 2–4 is being purified. For example, proteins having established molecular adhesion properties can be reversible fused to a BK beta subunit. With the appropriate ligand, a BK beta subunit 2–4 can be selectively adsorbed to a purification column and then freed from the column in a relatively pure form. The fused protein is then removed by enzymatic activity. Finally, a BK beta subunit 2–4 could be purified using immunoaffinity columns.

A. Purification of BK Beta Subunits 2–4 from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of a BK beta subunit inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. The BK beta subunit is separated from other bacterial proteins by standard separation techniques, e.g., with Ni-NTA agarose resin.

Alternatively, it is possible to purify BK beta subunits 2–4 from bacteria periplasm. After lysis of the bacteria, when the BK beta subunit is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying BK Beta Subunits 2–4

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of a BK beta subunit can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

A BK beta subunit can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of BK Beta Subunits 2–4

In addition to the detection of BK beta subunits 2–4 genes and gene expression using nucleic acid hybridization technology, one can also use immunoassays to detect BK beta subunits 2–4. Immunoassays can be used to qualitatively or quantitatively analyze BK beta subunits 2–4. A general overview of the applicable technology can be found in Harlow & Lane, *Antibodies: A Laboratory Manual* (1988).

A. Antibodies to BK Beta Subunits 2–4

Methods of producing polyclonal and monoclonal antibodies that react specifically with BK beta subunits 2–4 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising BK beta subunits 2–4 may be used to produce antibodies specifically reactive with the BK beta subunit. For example, recombinant BK beta subunit, BK beta 2, BK beta 3, or BK beta 4, or a antigenic fragment thereof such as the S1-S2 region, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-beta subunit proteins or even other related proteins from other organisms (e.g., other BK beta subunits), using a competitive binding immunoassay. Specific polyclonal antisera and monoclonal antibodies will usually bind with a $K_d$ of at least about 0.1 mM, more usually at least about 1 $\mu$M, preferably at least about 0.1 $\mu$M or better, and most preferably, 0.01 $\mu$M or better.

Once the specific antibodies against a BK beta subunit 2–4 are available, a BK beta subunit 2–4 can be detected by a variety of immunoassay methods. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

BK beta subunits 2–4 can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., $7^{th}$ ed. 1991). Immunological binding assays (or immunoassays) typically use an antibody that specifically binds to a protein or antigen of choice (in this case BK beta 2, BK beta 3, or BK beta 4, or an antigenic subsequence thereof). The antibody (e.g., anti-BK beta subunits 2, 3, or 4) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled the BK beta subunit or a labeled anti-BK beta subunit antibody. Alternatively, the labeling agent may be a third moiety, such a secondary antibody, that specifically binds to the antibody/BK beta 2–4 subunit complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting BK beta subunits in samples may be either competitive or noncompetitive. Noncompetitive immunoassays are assays in which the amount of antigen is directly measured. In one preferred "sandwich" assay, for example, an anti-BK beta subunit 2, 3, or 4 antibody can be bound directly to a solid substrate on which they are immobilized. These immobilized antibodies then capture the BK beta subunit present in the test sample. The BK beta subunit is thus immobilized and then bound by a labeling agent, such as a second BK beta subunit antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the BK beta subunit present in the sample is measured indirectly by measuring the amount of a known, added (exogenous) BK beta subunit displaced (competed away) from an anti-BK beta subunit antibody by the unknown BK beta subunit present in a sample. In one competitive assay, a known amount of the BK beta subunit is added to a sample and the sample is then contacted with an antibody that specifically binds to the BK beta subunit. The amount of exogenous BK beta subunit bound to the antibody is inversely proportional to the concentration of the BK beta subunit present in the sample. In a particularly preferred embodiment, the antibody is immobilized on a solid substrate. The amount of BK beta subunit bound to the antibody may be determined either by measuring the amount of BK beta subunit present in a BK beta subunit/antibody complex, or alternatively by measuring the amount of remaining uncomplexed protein. The amount of BK beta subunit may be detected by providing a labeled BK beta subunit molecule.

A hapten inhibition assay is another preferred competitive assay. In this assay a known BK beta subunit such as BK beta 3 is immobilized on a solid substrate. A known amount of anti-BK beta 3 antibody is added to the sample, and the sample is then contacted with the immobilized BK beta 3. The amount of anti-BK beta 3 antibody bound to the known immobilized BK beta 3 is inversely proportional to the amount of BK beta 3 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations for a BK beta subunit. 2, 3, or 4. For example, a protein at least partially encoded by SEQ ID NO:1, preferably including S1–S2 region, can be immobilized to a solid support. Other proteins, preferably other BK beta subunits such as BK beta 1, BK beta 3, or BK beta 4, are added to the assay so as to compete for binding of the antisera to the immobilized antigen. The ability of the added proteins to compete for binding of the antisera to the immobilized protein is compared to the ability of the BK beta subunit encoded by SEQ ID NO:1 compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of BK beta 2, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:1, or SEQ ID NO:3, or SEQ ID NO:5 that is required to inhibit 50% of binding, then the second protein is said to specifically bind to the polyclonal antibodies generated to the respective BK beta subunit immunogen.

Other Assay Formats

Western blot (immunoblot) analysis is used to detect and quantify the presence of the BK beta subunit in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the BK beta subunit. The anti-BK beta subunit antibodies specifically bind to the BK beta subunit on the solid support. These antibodies may be directly labeled or alternatively may be subsequently detected using labeled antibodies (e.g., labeled sheep anti-mouse antibodies) that specifically bind to the anti-BK beta subunit antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize the BK beta subunit, or secondary antibodies that recognize anti-BK beta subunit antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of Slo Channels Comprising BK Beta Subunits 2–4

A. Assays

BK beta subunits 2–4 and their alleles, interspecies homologs, polymorphic variants are auxiliary subunits of Slo family potassium channels. The activity of a Slo potassium channel comprising a BK beta subunit or monomer can be assessed using a variety of in vitro and in vivo assays, e.g., measuring voltage, current, measuring membrane potential, measuring ion flux, e.g., potassium or rubidium, measuring potassium concentration, measuring second messengers and transcription levels, measuring ligand binding, and using e.g., voltage-sensitive dyes, radioactive tracers, and patch-clamp electrophysiology.

Furthermore, such assays can be used to test for inhibitors and activators of channels comprising a BK beta subunit. Such modulators that target specific Slo channels differing in BK beta subunits composition are useful for treating a variety of diseases that alter excitation and secretion, such as CNS disorders such as migraines, hearing and vision problems, learning and memory problems, seizures, psychotic disorders, and as neuroprotective agents (e.g., to prevent stroke), and disorders of vascular and muscle tone, breathing (asthma), hormone secretion, spermatocyte differentiation and motility, lymphocyte differentiation and cell proliferation. These modulators are useful because they provide target specificity based on the expression patters of BK beta subunits. For example, modulators targeting Slo channels comprising BK beta 3 subunits, which are highly expressed in the CNS, are useful in treating excitatory and secretory disorders of the CNS. Modulators of Slo channels comprising BK beta 2 subunits would be useful in treating diseases related to glandular secretion and immune cell differentiation and proliferation. Such modulators are also useful for investigation of the channel diversity provided by BK beta subunits 2–4 and the regulation/modulation of channel activity provided by BK beta subunits 2–4.

Modulators of the Slo potassium channels are tested using biologically active BK beta subunits 2–4, either recombinant or naturally occurring. The BK beta subunit or a channel comprising such a subunit can be isolated, expressed in a cell, or expressed in a membrane derived from a cell. In such assays, each of the BK beta subunits is typically co-expressed with an alpha subunit of the Slo family such as Slo 1, Slo 2, or Slo 3. Modulation is tested using one of the in vitro or in vivo assays described above. Samples or assays that are treated with a potential Slo potassium channel inhibitor or activator are compared to control samples without the test compound, to examine the extent of modulation. Control samples (A Slo channel comprising a BK beta subunit, untreated with activators or inhibitors) are assigned a relative Slo potassium channel activity value of 100. Inhibition of channels comprising a BK beta subunit 2, 3, or 4 is achieved when the Slo potassium channel activity value relative to the control is about 90%, preferably 50%, more preferably 25%. Activation of channels comprising a BK beta subunit is achieved when the Slo potassium channel activity value relative to the control is 110%, more preferably 150%, more preferable 200% higher. Compounds that increase open probability of a channel comprising BK beta subunit 2, 3, or 4, by decreasing the probability of it being closed, increasing conductance through the channel, and allowing the passage of ions.

Changes in ion flux may be assessed by determining changes in polarization (i.e., electrical potential) of the cell or membrane expressing the Slo potassium channel comprising a BK beta subunit 2, 3, or 4. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radiolabeled rubidium flux assays and fluorescence assays using voltage-sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)). Assays for compounds capable of inhibiting or increasing potassium flux through the channel proteins comprising a BK beta subunit 2, 3, or 4 can be performed by application of the compounds to a bath solution in contact with and comprising cells having an channel of the present invention (see, e.g., Blatz et al., *Nature* 323:718–720 (1986); Park, *J. Physiol.* 481:555–570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of cations such as potassium or rubidium ions. The cations can be measured in a variety of standard ways. They can be measured directly by concentration changes of the ions or indirectly by membrane potential or by radiolabeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as [$Ca^{2+}$].

Preferably, a BK beta subunit 2, 3, or 4 that is a part of the Slo potassium channel used in the assay will be selected from a subunit having a sequence of SEQ ID NO:1, SEQ ID NO:3, or SEQ ID NO:5 or a conservatively modified variant thereof. Alternatively, the BK beta subunit of the assay will be derived from a eukaryote and include an amino acid subsequence having amino acid sequence identity to the BK beta subunit. Generally, the amino acid sequence identity will be at least about 70%, preferably at least 80%, most preferably at least 90–95%. Alternatively, the BK beta subunit of the assay is derived from a eukaryote and include an amino acid subsequence having amino acid sequence identity to the S1–S2 region of the BK beta subunit. Generally, the amino acid sequence identity will be at least 70%, preferably at least 80%, and most preferably at least 90–95%.

BK beta subunit 2, 3, or 4 polymorphic variants, alleles, and interspecies homologs will generally confer substantially similar properties on a channel, e.g., modulating the activity of Slo channels comprising such a subunit, as described above. Furthermore, Slo family potassium channels comprising such putative BK beta subunit homologs should respond to modulatory compounds in a manner similar to Slo potassium channels comprising BK beta 2, 3, or 4. In one embodiment, a cell or cell membrane in which has been expressed a putative BK beta homolog, allele, or interspecies homolog is assayed with a compound that modulates Slo family potassium channels. In one embodiment, compounds with known modulatory activity for Slo family potassium channels comprising known BK beta subunits are used in assays to identify putative BK beta subunit homologs.

B. Modulators

The compounds tested as modulators of Slo channels comprising a BK beta subunit can be any small chemical compound, or a biological entity, such as a protein, sugar, nucleic acid or lipid. Alternatively, modulators can be genetically altered versions of a BK beta subunit. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer.*

Chem. Soc. 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274: 1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a Slo channel comprising a BK beta subunit is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100–about 1500 different compounds. It is possible to assay several different plates per day; assay screens for up to about 6,000–20,000 different compounds is possible using the integrated systems of the invention.

VII. Computer Assisted Drug Design Using BK Beta Subunits 2–4

Yet another assay for compounds that modulate channels comprising BK beta subunits 2, 3, or 4 involves computer assisted drug design, in which a computer system is used to generate a three-dimensional structure of the BK subunit based on the structural information encoded by the amino acid sequence. The amino acid sequence entered into the system interacts directly and actively with a preestablished algorithm in a computer program to yield secondary, tertiary, and quaternary structural models of the protein. The models of the protein structure are then examined to identify regions of the structure that have the ability to bind, e.g., ligands or other potassium channel subunits. These regions are then used to identify ligands that bind to the protein or region where the BK beta subunit interacts with other potassium channel subunits. Information generated by the computer system, e.g., structures, sequence comparisons and the like, are saved on computer readable substrates.

The three-dimensional structural model of the protein is generated by entering channel protein amino acid sequences of at least 10 amino acid residues or corresponding nucleic acid sequences encoding a BK beta subunit 2, 3, or 4 into the computer system. The amino acid sequence of each of the monomers is selected from the group consisting of SEQ ID NO:1, SEQ ID NO:3, and SEQ ID NO:5, for BK beta 2, BK beta 3, and BK beta 4, respectively, and a conservatively modified versions thereof. The amino acid sequence represents the primary sequence or subsequence of each of the proteins, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the channel protein is then generated by the interaction of the amino acid sequence and the computer system, using software known to those of skill in the art.

The amino acid sequence represents a primary structure that encodes the information necessary to form the secondary, tertiary and quaternary structure of the monomer and the potassium channel protein comprising multiple monomers. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the BK beta subunit protein to identify ligands that bind to the BK beta subunit. Binding affinity between the protein and ligands is determined using energy terms to determine which ligands have an enhanced probability of binding to the protein.

Computer systems are also used to screen for mutations, polymorphic variants, alleles and interspecies homologs of BK beta subunit genes. Such mutations can be associated with disease states. Once the variants are identified, diagnostic assays can be used to identify patients having such mutated genes associated with disease states. Identification of the mutated BK beta subunit genes involves receiving input of a first nucleic acid, selected from the group consisting of SEQ ID NO:2, SEQ ID NO:4, and SEQ ID NO:6, or an amino acid sequence encoding the BK beta subunit, selected from the group consisting of SEQ ID NO:1, SEQ ID NO:3, and SEQ ID NO:5, and a conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in the BK beta subunit genes, and mutations associated with disease states.

BK beta subunits 2–4 and the Slo potassium channels comprising these BK beta subunits can be used with high density oligonucleotide array technology (e.g., GeneChip™) to identify homologs and polymorphic variants of the BK beta subunits in this invention. In the case where the homologs being identified are linked to a known disease, they can be used with high density oligonucleotide array technology as a diagnostic tool in detecting the disease in a biological sample (see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998)).

VIII. Cellular Transfection and Gene Therapy

The present invention provides the nucleic acids of BK beta subunits 2–4 for the transfection of cells in vitro and in vivo. These nucleic acids can be inserted into any of a number of well known vectors for the transfection of target cells and organisms as described below. The nucleic acids are transfected into cells, ex vivo or in vivo, through the interaction of the vector and the target cell. The nucleic acids encoding BK beta subunits 2, 3, or 4, under the control of a promoter, then expresses a BK beta subunit of the present invention, thereby mitigating the effects of absent, partial inactivation, or abnormal expression of the BK beta subunit gene.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Mulligan, *Science* 926–932 (1993); Dillon, *TIBTECH* 11:167–175 (1993); Miller, *Nature* 357: 455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1:13–26 (1994)).

Delivery of the gene or genetic material into the cell is the first critical step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Dillon, *TIBTECH* 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* Doerfler and Böhm (eds) (1995); and Yu et al., *Gene Therapy* 1:13–26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251–3260 (1985); Tratschin, et al., *Mol. Cell. Biol.* 4:2072–2081 (1984); Hermonat & Muzyczka, *Proc. Natl. Acad. Sci. U.S.A.* 81:6466–6470 (1984); and Samulski et al., *J. Virol.* 63:03822–3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048–305 (1995); Kohn et al., *Nat. Med.* 1: 1017–102 (1995); Malech et al., *Proc. Natl. Acad. Sci. U.S.A.* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors. (Ellem et al., *Immunol Immunother.* 44(1):10–20 (1997); Dranoff et al., *Hum. Gene Ther.* 1:111–2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702–3 (1998), Kearns et al., *Gene Ther.* 9:748–55 (1996)).

Replication-deficient recombinant adenoviral vectors (Ad) are predominantly used transient expression gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Rosenecker et al., *Infection* 24:1 5–10 (1996); Sterman et al., *Hum. Gene Ther.* 9:7 1083–1089 (1998); Welsh et al., *Hum. Gene Ther.* 2:205–18 (1995); Alvarez et al., *Hum. Gene Ther.* 5:597–613 (1997); Topfet al., *Gene Ther.* 5:507–513 (1998); Sterman et al., *Hum. Gene Ther.* 7:1083–1089 (1998).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

IX. Pharmaceutical Compositions

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17$^{th}$ ed., 1989).

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampules and vials.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the Slo family potassium channel comprising a BK beta subunit, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

X. Kits

BK beta subunits 2–4 and their homologs are useful tools for examining expression and regulation of Slo family potassium channels. Reagents that specifically hybridize to nucleic acids encoding BK beta subunit 2, 3, or 4, such as BK beta subunits 2–4 probes and primers, and reagents that specifically bind to BK beta subunits 2–4 protein, e.g., antibodies, are used to examine expression and regulation.

Nucleic acid assays for the presence of BK beta subunits 2–4 DNA and RNA in a sample include numerous techniques are known to those skilled in the art, such as Southern analysis, northern analysis, dot blots, RNase protection, S1 analysis, amplification techniques such as PCR and LCR, high density oligonucleotide array analysis, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, a BK beta subunit can be detected with the various immunoassay techniques described above. The test sample is typically compared to both a positive control (e.g., a sample expressing recombinant BK beta subunit 2, 3, or 4) and a negative control.

The present invention also provides for kits for screening modulators of the potassium channels. Such kits can be prepared from readily available materials and reagents. For example, such kits can comprise any one or more of the following materials: BK beta subunits 2, 3, and/or 4, reaction tubes, and instructions for testing the activities of Slo potassium channels comprising a BK beta subunit. A wide variety of kits and components can be prepared according to the present invention, depending upon the intended user of the kit and the particular needs of the user. For example, the kit can be tailored for in vitro or in vivo assays for measuring the activity of a Slo family potassium channel comprising a BK beta subunit.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Isolation of Nucleic Acids Encoding BK Beta 2 and Functional Analysis of Potassium Channels Containing BK Beta 2

Using PCR and primers, according to standard conditions, BK beta 2 is amplified from a human testis cDNA library. The following primers are used for amplification of BK beta 2:

(1) 5-ATGACAGCCTTTCCTGCCTCAGGGAAG-3     (SEQ ID NO:7)

(2) 5-AGATTTCTCTGCTCTTCCTTTGCTCCTCC-3   (SEQ ID NO:8)

(3) 5-GGCTGGCTGGACTGTAGAAGCATG-3        (SEQ ID NO:9)

(4) 5-GAGGCTGTCCAGATAAATCCCAAGTGC-3     (SEQ ID NO:10)

(5) 5-GGACTGAGAAGCCCATCATGGCAAACC-3     (SEQ ID NO:11)

Primers (1) and (2) are used together to amplify the entire coding sequence. Primers (1) and (3) are used to amplify the 5' half of the coding sequence, while primers (2) and (4) are used to amplify the 3' half. Primers (1) and (5) are used as a set of oligos that may amplify any splice variants since they are in the same exon. Primers (3) and (4) might also be good choices for this purpose.

PCR conditions are as follows: 95 degrees for 30 seconds, 68–58 degrees for 15 seconds, 72 degrees for 45 seconds. The reaction is run for 40 cycles.

The PCR products are subcloned into plasmids and sequenced according to standard techniques. The nucleotide and amino acid sequences of BK beta 2 are provided, respectively, in SEQ ID NO:2 and SEQ ID NO:1.

BK beta 2 monomer is co-expressed with a Slo alpha subunit monomer according to standard methodology to demonstrate its ability to associate with potassium channels made by alpha subunits the Slo potassium channel family. Changes in Slo potassium channel activity are observed by measuring their current/voltage relationship at given calcium concentrations.

BK beta 2 expression patterns were analyzed using northern blots and mRNA dot blots (FIG. 2). BK beta expression was high in placenta, while lower levels of expression were detected in a variety of tissues including substantia nigra, spinal cord, lung, prostate, testis, pancreas, stomach, small intestine, pituitary gland, adrenal gland, thyroid, salivary gland, mammary gland, spleen, thymus, lymph node, bone marrow, fetal liver, fetal spleen, and fetal lung. Trace levels of express were detected in a variety of nervous and peripheral tissues (FIG. 2).

Example II

Isolation of Nucleic Acids Encoding BK Beta 3 and Functional Analysis of Potassium Channels Containing BK Beta 3

Using PCR and primers, according to standard conditions, BK beta 3 is amplified from a human hippocampus cDNA library. The following primers are used for amplification of BK beta 3:

(1) 5-ATGGCGAAGCTCCGGGTGGCTTAC-3        (SEQ ID NO:12)

(2) 5-TTAAGAGAACTTGCGCTTCTTCATGG-3      (SEQ ID NO:13)

(3) 5-GATGTGCTTCTGCATCGCACTCATG-3       (SEQ ID NO:14)

Primers (1) and (2) are used together to amplify the entire coding sequence. Primers (2) and (3) are used to amplify the 3' end of the coding sequence. They are in the same exon.

PCR conditions are as follows: 95 degrees for 30 seconds, 68–58 degrees for 15 seconds, 72 degrees for 45 seconds. The reaction is run for 40 cycles.

The PCR products are subcloned into plasmids and sequenced according to standard techniques. The nucleotide and amino acid sequences of BK beta 3 are provided, respectively, in SEQ ID NO:4 and SEQ ID NO:3.

BK beta 3 monomer is co-expressed with a Slo alpha subunit monomer according to standard methodology to demonstrate its ability to associate with potassium channels made by alpha subunits the Slo potassium channel family. Changes in Slo potassium channel activity are observed by measuring their current/voltage relationship at given calcium concentrations.

BK beta 3 expression patterns were analyzed using northern blots and mRNA dot blots (FIG. 2). It is highly expressed in the brain and was expressed in all neuronal tissues that were tested. Its expression was especially high in the hippocampus, putamen, substantia nigra, temporal lobe, thalamus, nucleus accumbens, cerebral cortex, amygdala, occipital lobe and fetal brain, with lower expression levels in the cerebellum and medulla.

BK beta 3 was also expressed at moderate to low levels in several peripheral tissues, such as adrenal gland, fetal heart, fetal lung, small intestine, fetal kidney, appendix, lung, placenta, thyroid, ovary, pituitary, and prostate. There were trace levels of expression in heart, aorta, colon, bladder, uterus, stomach, testis, salivary gland, kidney, thymus, and spleen.

Figure 3A:
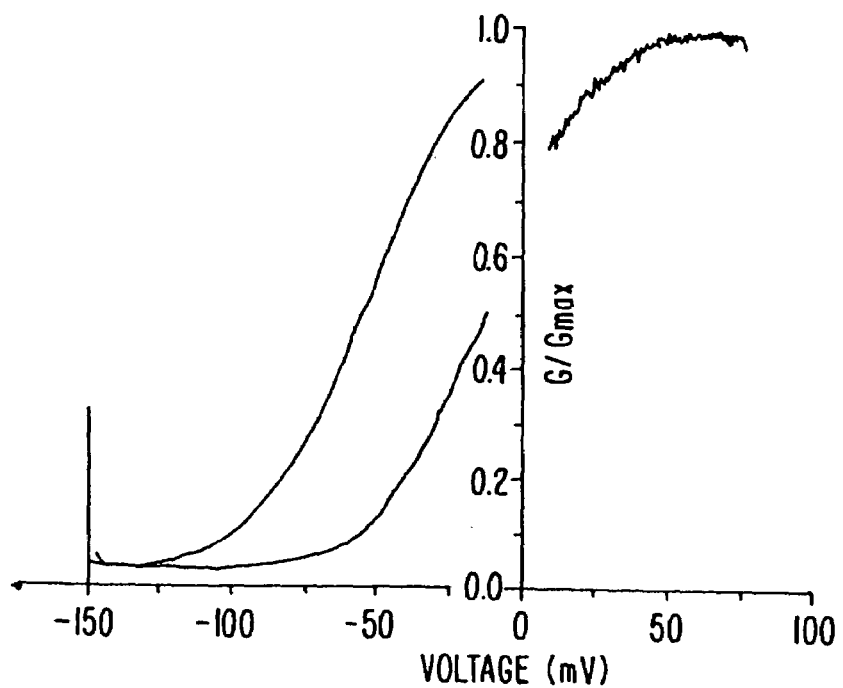
FIG. 3A: Normalized conductance-voltage curves for hSlo1 in the absence (dashed lines) or the presence (solid lines) of BK beta 3. Data is from inside-out membrane patches of *Xenopus* oocytes expressing Slo1. Conductance-voltage curves were derived from the current voltage relationship according to: G=I/V-Ek, where Ek was omV. Current voltage relationships were determined with slow voltage ramps (1.5 s) from –150 mV to +100 mV. Free calcium concentration was calculated to be 7 $\mu$M.
Figure 3B:
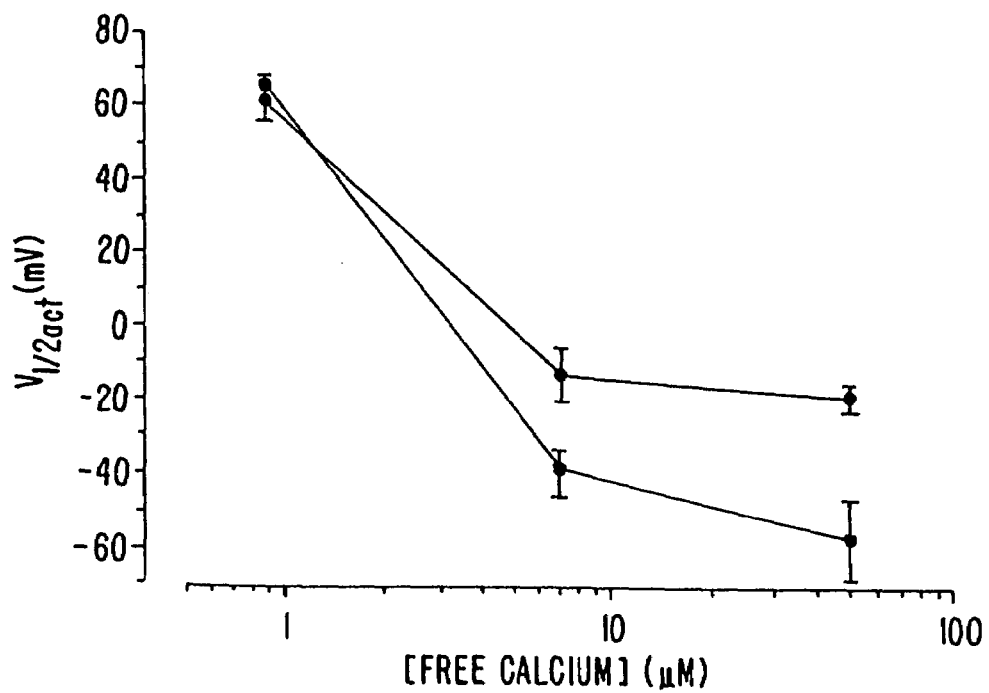
FIG. 3B: V1/2 activation values were calculated from G-V as shown in FIG. 3A. Mean V1/2act +/–sem values are plotted against calculated free calcium concentration for hSlo1 in the absence (squares) and presence (diamonds) of BK beta 3. Symbols are means of 3–4 patches per point.
Figure 4A:
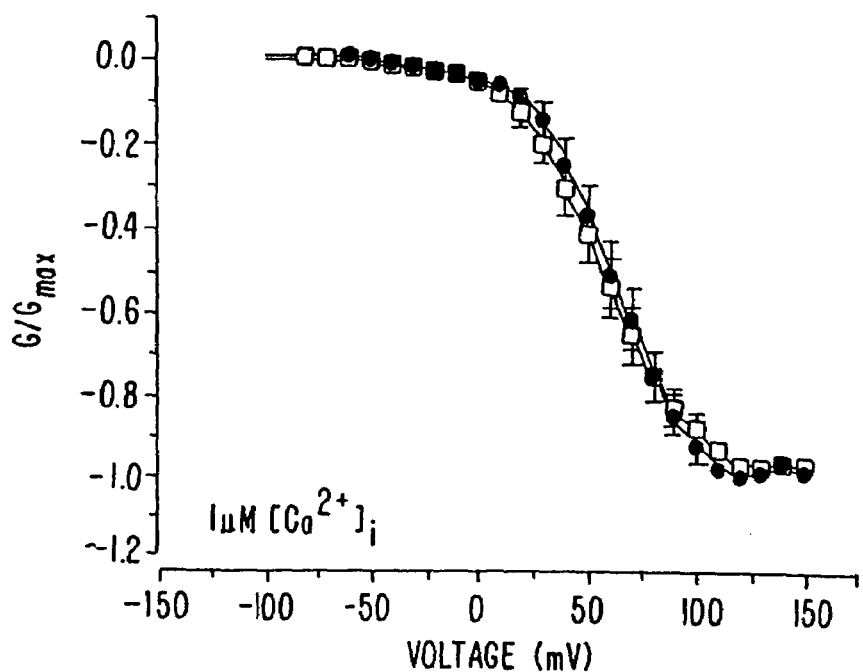
FIG. 4: Effect of BK beta 3 on voltage- and calcium dependent activation of Slo-1. Conductance-voltage relationships were constructed by measuring the deactivating tail current amplitude at –50 mV following a series of 500 ms depolarizing steps (–100 mV to +150 mV in 10 mV increments) from a holding potential of –140 mV. Activation curves were generated by plotting normalized tail current amplitude against the step potential, fitted with a Boltzman distribution and are plotted in FIGS. 4A–4C for Slo-1 alone (solid circles) and Slo-1 co-expressed with BK beta 3 (open squares). The voltages for half-maximal activation (V1/2act, mV) were determined from fitted data and are plotted against free calcium concentration in FIG. 4D. BK beta 3 had no significant effect on the voltage-dependence of Slo-1 activation in the presence of low Ca2+ concentrations (10 $\mu$M or less, FIGS. 4A, B and D). In the presence of 50 $\mu$M free Ca2+ however, BK beta 3 produced a small, but significant (approximately 15 mV), leftward shift in the Slo-1 activation curve (FIGS. 4C, D). Symbols represent the mean of 8–12 experiments, vertical lines represent the S.E.M. * indicates P<0.05, 2-tail t-test.
Figure 4B:
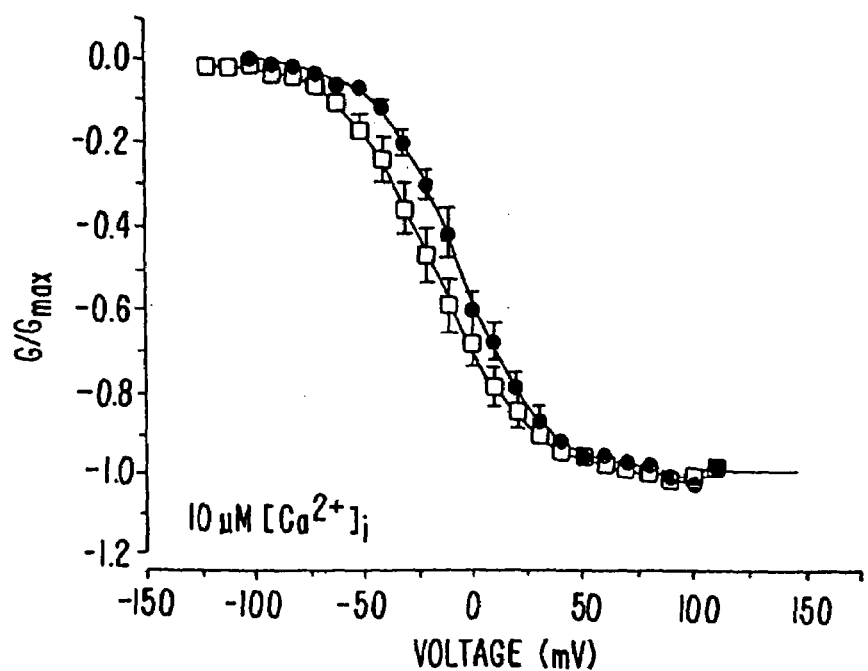
Figure 4C:
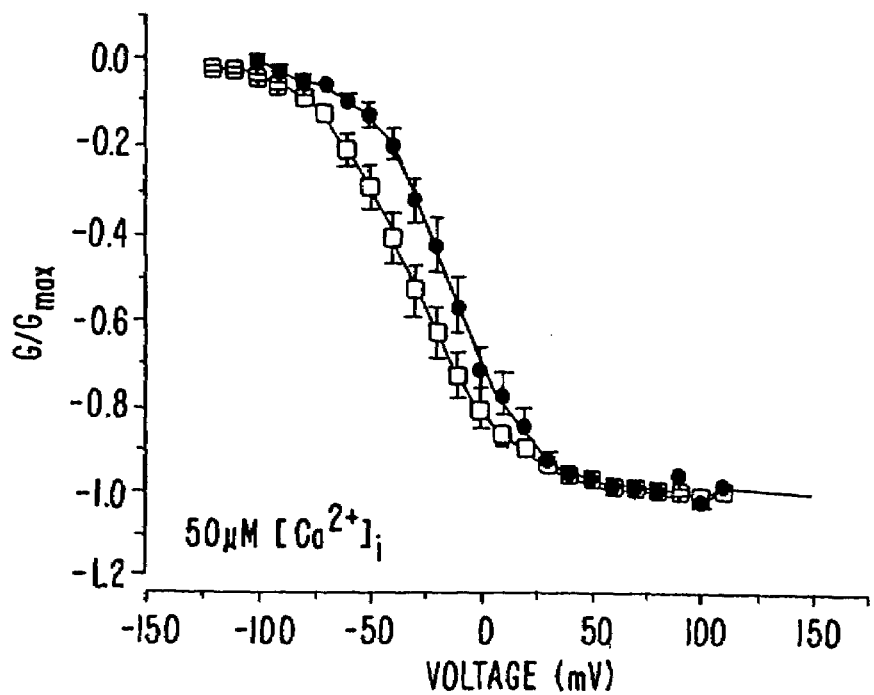
Figure 4D:
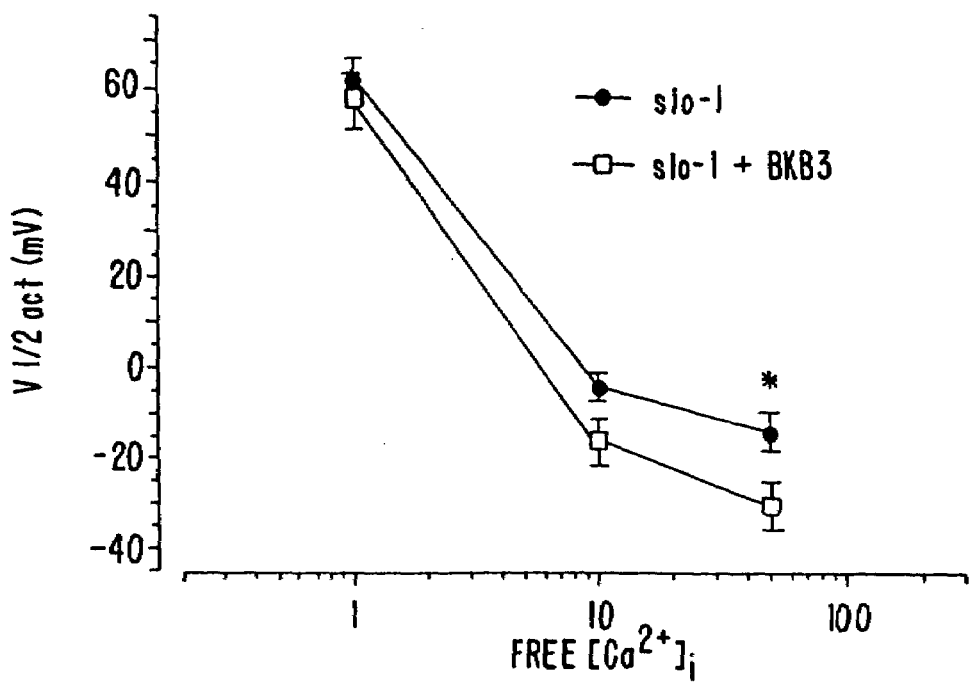

When co-expressed with human Slo, BK beta 3 causes a hyperpolarized shift in the activation curve vs. voltage curve when compared to Slo1 expressed alone (FIG. 3). Furthermore, when coexpressed with Slo1, BK beta 3 slows the activation of Slo channels and causes a small hyperpolarized shift in the activation vs. voltage curve that is most pronounced at higher calcium concentrations (see FIGS. 4–5).

In addition, BK beta 3 greatly reduces the sensitivity of Slo1 channels to charybdotoxin (FIG. 6). When expressed alone, Slo1 channels are almost completely blocked by 100 nM charybdotoxin. However, when expressed with BK beta 3, the Slo1 current is virtually unblocked by 100 nM charybdotoxin. The Slo1/BKB3 channels have similar properties to the Type II BK channels that have been identified in mammalian brain (Reinhart et al., Neuron 2:1031–1041 (1989)), which also have slowed activation kinetics and resistance to charybdotoxin block. It is therefore likely that modulators of mammalian type II BK channels can be identified by screening for compounds that modulate heterologously expressed channels consisting of Slo1 and BK beta 3 subunits.

Example III

Isolation of Nucleic Acids Encoding BK Beta 4 and Functional Analysis of Potassium Channels Containing BK Beta 4

Using PCR and primers, according to standard conditions, BK beta 4 is amplified from a human heart cDNA library. The following primers are used for amplification of BK beta 4:

(1) 5-AAGATGTCGATATGGACCAGTGGCC-3    (SEQ ID NO:15)

(2) 5-TTATCTATTGATCCGTTGGATCCTCTC-3  (SEQ ID NO:16)

(3) 5-CTCCTTCAGCTGTCCTCCAGACTGC-3    (SEQ ID NO:17)

(4) 5-GTCCCAGTAGAATAGCTCGGTCCTC-3    (SEQ ID NO:18)

Primers (1) and (2) are used together to amplify the entire coding sequence. Primers (1) and (4) are used to amplify the 5' end of the coding sequence. Primers (2) and (3) are used to amplify the 3' half of coding.

PCR conditions are as follows: 95 degrees for 30 seconds, 68–58 degrees for 15 seconds, 72 degrees for 45 seconds. The reaction is run for 40 cycles.

The PCR products are subcloned into plasmids and sequenced according to standard techniques. The nucleotide and amino acid sequences of BK beta 4 are provided, respectively, in SEQ ID NO:6 and SEQ ID NO:5.

BK beta 4 monomer is co-expressed with a Slo alpha subunit monomer according to standard methodology to demonstrate its ability to associate with potassium channels made by alpha subunits the Slo potassium channel family. Changes in Slo potassium channel activity are observed by measuring their current/voltage relationship at given calcium concentrations.

BK beta 4 expression patterns were analyzed using northern blots and mRNA dot blots (FIG. 2). The highest expression of BK beta 4 was found in fetal kidney. Moderate levels of expression were also present in ovary and pituitary gland. Low levels of expression were found in fetal lung, heart, fetal brain, occipital lobe, substantia nigra, thalamus, nucleus accumbeus, and putamen. Trace levels were found in amygdala, caudate, cerebral cortex, frontal lobe, temporal lobe, hippocampus, spinal cord, uterus, stomach, pancreas, kidney, trachea, fetal heart, and fetal spleen.

Figure 7:
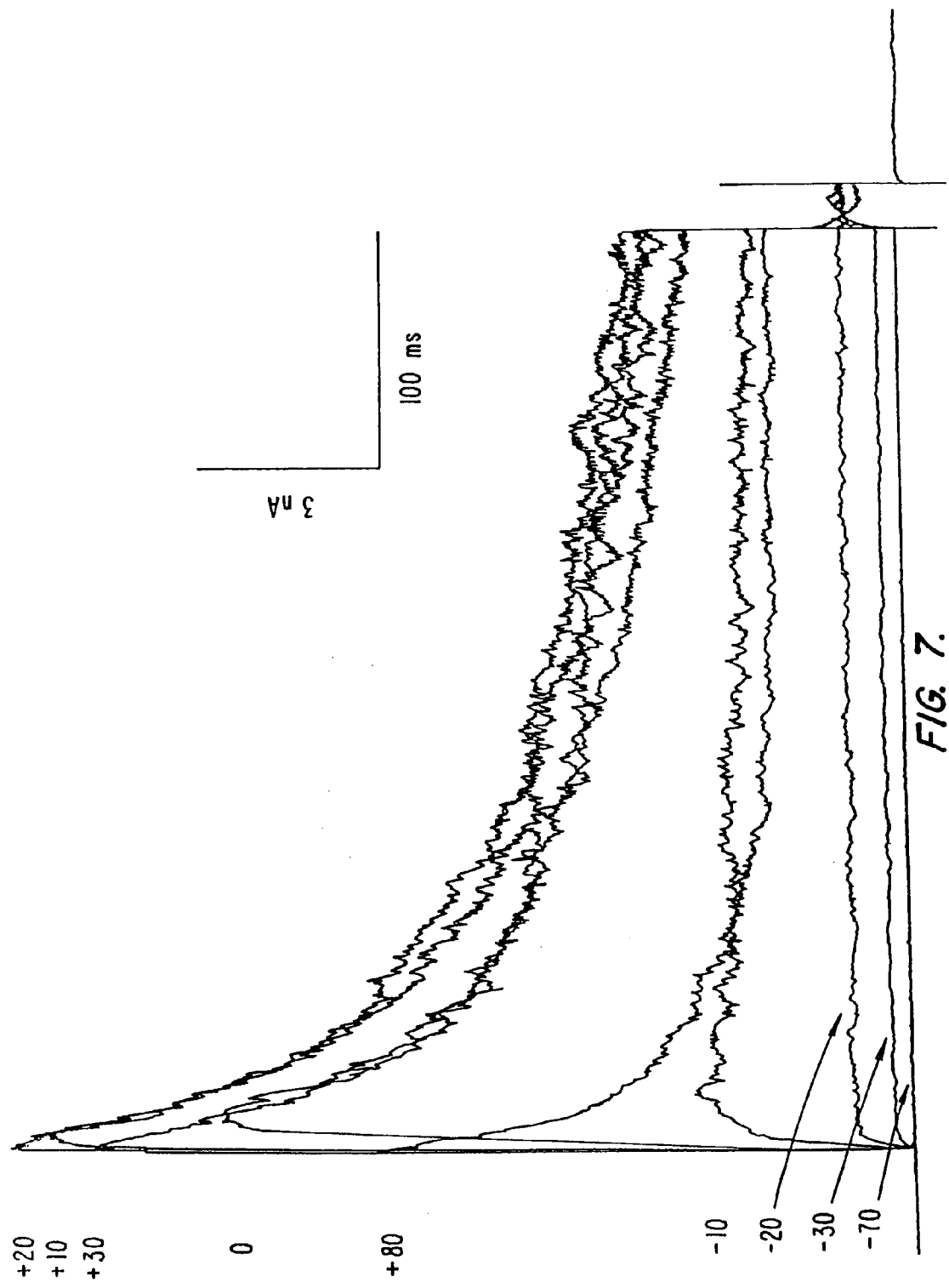
FIG. 7. Whole-cell recording from a CHO cell cotransfected with BKB4 and Slo1. Cell was stepped to the indicated voltages for 400 ms followed by a step to –20 mV for 40 ms, from a holding potential was –80 mV. Unlike homomeric Slo1 channels, the BKB4+Slo1 channels inactivate rapidly. Pipette solution contained (mM): 40 KCl, 100 KF, 5 NaCl, 1 MgCl2, 5 glucose, 10 HEPES, pH=7.4. Extracellular bath solution contained (mM): 138 NaCl, 2 CaCl2, 5.4 KCl, 1 MgCl2, 10 glucose, 10 HEPES, pH=7.4.

When coexpressed with human Slo1, BK beta 4 causes inactivation (FIG. 7). At a given calcium concentration, the rate of inactivation increases with increasing depolarization. Because this inactivation limits the timecourse of potassium efflux through Slo channels, BK beta 4 expression may exert a profound effect on how the slo currents are able to modulate excitability and secretion.

What is claimed is:

1. An isolated nucleic acid encoding a beta subunit polypeptide of a potassium channel, wherein the beta subunit polypeptide:
   (i) forms, with four alpha subunit polypeptides, a slo potassium channel; and
   (ii) comprises an amino acid sequence that has greater than 80% identity to SEQ ID NO: 5, and wherein said beta subunit polypeptide slows activation of the slo current.

2. The isolated nucleic acid of claim 1, wherein the nucleic acid encodes a beta subunit polypeptide that specifically binds to polyclonal antibodies generated against a polypeptide comprising an amino acid sequence of SEQ ID NO: 5.

3. The isolated nucleic acid of claim 1, wherein the nucleic acid encodes a polypeptide comprising an amino acid sequence of SEQ ID NO:5.

4. The isolated nucleic acid sequence of claim 1, wherein the nucleic acid comprises a nucleotide sequence of SEQ ID NO:6.

5. An expression vector comprising the nucleic acid of claim 1.

6. An isolated host cell transfected with the vector of claim 5.

* * * * *

SEQUENCE LISTING

<160> NUMBER OF SEQ ID NOS: 19

<210> SEQ ID NO 1
<211> LENGTH: 257
<212> TYPE: PRT
<213> ORGANISM: Homo sapiens
<220> FEATURE:
<223> OTHER INFORMATION: BK beta 2

<400> SEQUENCE: 1

Met Thr Ala Phe Pro Ala Ser Gly Lys Lys Arg Glu Thr Asp Tyr Ser
 1               5                  10                  15

Asp Gly Asp Pro Leu Asp Val His Lys Arg Leu Pro Ser Ser Thr Gly
                20                  25                  30

Glu Asp Arg Ala Val Met Leu Gly Phe Ala Met Met Gly Phe Ser Val
            35                  40                  45

Leu Met Phe Phe Leu Leu Gly Thr Thr Ile Leu Lys Pro Phe Met Leu
        50                  55                  60

Ser Ile Gln Arg Glu Glu Ser Thr Cys Thr Ala Ile His Thr Asp Ile
    65                  70                  75                  80

Met Asp Asp Trp Leu Asp Cys Ala Phe Thr Cys Gly Val His Cys His
                85                  90                  95

Gly Gln Gly Lys Tyr Pro Cys Leu Gln Val Phe Val Asn Leu Ser His
                100                 105                 110

```
Pro Gly Gln Lys Ala Leu Leu His Tyr Asn Glu Glu Ala Val Gln Ile
        115                 120                 125

Asn Pro Lys Cys Phe Tyr Thr Pro Lys Cys His Gln Asp Arg Asn Asp
    130                 135                 140

Leu Leu Asn Ser Ala Leu Asp Ile Lys Glu Phe Phe Asp His Lys Asn
145                 150                 155                 160

Gly Thr Pro Phe Ser Cys Phe Tyr Ser Pro Ala Ser Gln Ser Glu Asp
                165                 170                 175

Val Ile Leu Ile Lys Lys Tyr Asp Gln Met Ala Ile Phe His Cys Leu
            180                 185                 190

Phe Trp Pro Ser Leu Thr Leu Gly Gly Ala Leu Ile Val Gly Met
            195                 200                 205

Val Arg Leu Thr Gln His Leu Ser Leu Leu Cys Glu Lys Tyr Ser Thr
    210                 215                 220

Val Val Arg Asp Glu Val Gly Gly Lys Val Pro Tyr Ile Glu Gln His
225                 230                 235                 240

Gln Phe Lys Leu Cys Ile Met Arg Arg Ser Lys Gly Arg Ala Glu Lys
                245                 250                 255

Ser
```

<210> SEQ ID NO 2
<211> LENGTH: 774
<212> TYPE: DNA
<213> ORGANISM: Homo sapiens
<220> FEATURE:
<223> OTHER INFORMATION: BK beta 2

<400> SEQUENCE: 2

```
atgacagcct ttcctgcctc agggaagaag agagagacag actacagtga tggagaccca      60
ctagatgtgc acaagaggct gccatccagt actggagagg accgagccgt gatgctgggg     120
tttgccatga tgggcttctc agtcctaatg ttcttcttgc tcggaacaac cattctaaag     180
cctttatgc tcagcattca gagagaagaa tcgacctgca ctgccatcca cacagatatc     240
atggacgact ggctggactg tgccttcacc tgtggtgtgc actgccacgg tcaggggaag     300
tacccgtgtc ttcaggtgtt tgtgaacctc agccatccag gtcagaaagc tctcctacat     360
tataatgaag aggctgtcca gataaatccc aagtgctttt acacacctaa gtgccaccaa     420
gatagaaatg atttgctcaa cagtgctctg gacataaaag aattcttcga tcacaaaaat     480
ggaaccccct tttcatgctt ctacagtcca gccagccaat ctgaagatgt cattcttata     540
aaaaagtatg accaaatggc tatcttccac tgtttatttt ggccttcact gactctgcta     600
ggtggtgccc tgattgttgg catggtgaga ttaacacaac cctgtccctt actgtgtgaa     660
aaatatagca ctgtagtcag agatgaggta ggtggaaaag tacctatat agaacagcat     720
cagttcaaac tgtgcattat gaggaggagc aaaggaagag cagagaaatc ttaa          774
```

<210> SEQ ID NO 3
<211> LENGTH: 210
<212> TYPE: PRT
<213> ORGANISM: Homo sapiens
<220> FEATURE:
<223> OTHER INFORMATION: BK beta 3

<400> SEQUENCE: 3

```
Met Ala Lys Leu Arg Val Ala Tyr Glu Tyr Thr Glu Ala Glu Asp Lys
1               5                   10                  15

Ser Ile Arg Leu Gly Leu Phe Leu Ile Ile Ser Gly Val Val Ser Leu
```

```
                  20                  25                  30
Phe Ile Phe Gly Phe Cys Trp Leu Ser Pro Ala Leu Gln Asp Leu Gln
             35                  40                  45
Ala Thr Glu Ala Asn Cys Thr Val Leu Ser Val Gln Gln Ile Gly Glu
 50                  55                  60
Val Phe Glu Cys Thr Phe Thr Cys Gly Ala Asp Cys Arg Gly Thr Ser
 65                  70                  75                  80
Gln Tyr Pro Cys Val Gln Val Tyr Val Asn Asn Ser Glu Ser Asn Ser
                 85                  90                  95
Arg Ala Leu Leu His Ser Asp Glu His Gln Leu Leu Thr Asn Pro Lys
            100                 105                 110
Cys Ser Tyr Ile Pro Pro Cys Lys Arg Glu Asn Gln Lys Asn Leu Glu
            115                 120                 125
Ser Val Met Asn Trp Gln Gln Tyr Trp Lys Asp Glu Ile Gly Ser Gln
            130                 135                 140
Pro Phe Thr Cys Tyr Phe Asn Gln His Gln Arg Pro Asp Asp Val Leu
145                 150                 155                 160
Leu His Arg Thr His Asp Glu Ile Val Leu Leu His Cys Phe Leu Trp
                165                 170                 175
Pro Leu Val Thr Phe Val Val Gly Val Leu Ile Val Val Leu Thr Ile
            180                 185                 190
Cys Ala Lys Ser Leu Ala Val Lys Ala Glu Ala Met Lys Lys Arg Lys
            195                 200                 205
Phe Ser
    210

<210> SEQ ID NO 4
<211> LENGTH: 633
<212> TYPE: DNA
<213> ORGANISM: Homo sapiens
<220> FEATURE:
<223> OTHER INFORMATION: BK beta 3

<400> SEQUENCE: 4
atggcgaagc tccgggtggc ttacgagtac acggaagccg aggacaagag catccggctc      60
ggcttgtttc tcatcatctc cggcgtcgtg tcgctcttca tcttcggctt ctgctggctg     120
agtcccgcgc tgcaggatct gcaagccacg gaggccaatt gcacggtgct gtcggtgcag     180
cagatcggcg aggtgttcga gtgcaccttc acctgtggcg ccgactgcag gggcacctcg     240
cagtacccct gcgtccaggt ctacgtgaac aactctgagt ccaactctag gcgcgctgctg    300 cacagcgacg agcaccagct cctgaccaac cccaagtgct cctatatccc tccctgtaag     360
agagaaaatc agaagaattt ggaaagtgtc atgaattggc aacagtactg gaaagatgag     420
attggttccc agccatttac ttgctatttt aatcaacatc aaagaccaga tgatgtgctt     480
ctgcatcgca ctcatgatga gattgtcctc ctgcattgct cctctggcc cctggtgaca      540 tttgtggtgg gcgttctcat tgtggtcctg accatctgtg ccaagagctt ggcggtcaag     600
gcggaagcca tgaagaagcg caagttctct taa                                  633

<210> SEQ ID NO 5
<211> LENGTH: 235
<212> TYPE: PRT
<213> ORGANISM: Homo sapiens
<220> FEATURE:
<223> OTHER INFORMATION: BK beta 4

<400> SEQUENCE: 5
```

```
Met Ser Ile Trp Thr Ser Gly Arg Thr Ser Ser Tyr Arg His Asp
  1               5                  10                 15

Glu Lys Arg Asn Ile Tyr Gln Lys Ile Arg Asp His Asp Leu Leu Asp
                 20                  25                  30

Lys Arg Lys Thr Val Thr Ala Leu Lys Ala Gly Glu Asp Arg Ala Ile
             35                  40                  45

Leu Leu Gly Leu Ala Met Met Val Cys Ser Ile Met Met Tyr Phe Leu
         50                  55                  60

Leu Gly Ile Thr Leu Leu Arg Ser Tyr Met Gln Ser Val Trp Thr Glu
 65                  70                  75                  80

Glu Ser Gln Cys Thr Leu Leu Asn Ala Ser Ile Thr Glu Thr Phe Asn
                 85                  90                  95

Cys Ser Phe Ser Cys Gly Pro Asp Cys Trp Lys Leu Ser Gln Tyr Pro
                100                 105                 110

Cys Leu Gln Val Tyr Val Asn Leu Thr Ser Ser Gly Glu Lys Leu Leu
             115                 120                 125

Leu Tyr His Thr Glu Glu Thr Ile Lys Ile Asn Gln Lys Cys Ser Tyr
        130                 135                 140

Ile Pro Lys Cys Gly Lys Asn Phe Glu Glu Ser Met Ser Leu Val Asn
145                 150                 155                 160

Val Val Met Glu Asn Phe Arg Lys Tyr Gln His Phe Ser Cys Tyr Ser
                165                 170                 175

Asp Pro Glu Gly Asn Gln Lys Ser Val Ile Leu Thr Lys Leu Tyr Ser
            180                 185                 190

Ser Asn Val Leu Phe His Ser Leu Phe Trp Pro Thr Cys Met Met Ala
        195                 200                 205

Gly Gly Val Ala Ile Val Ala Met Val Lys Leu Thr Gln Tyr Leu Ser
        210                 215                 220

Leu Leu Cys Glu Arg Ile Gln Arg Ile Asn Arg
225                 230                 235
```

<210> SEQ ID NO 6
<211> LENGTH: 707
<212> TYPE: DNA
<213> ORGANISM: Homo sapiens
<220> FEATURE:
<223> OTHER INFORMATION: BK beta 4

<400> SEQUENCE: 6

```
atgtcgatat ggaccagtgg ccggacctct tcatcttata gacatgatga aaaagaaat     60 atttaccaga aaatcaggga ccatgacctc ctggacaaaa ggaaaacagt cacagcactg    120
aaggcaggag aggaccgagc tattctcctg ggactggcta tgatggtgtg ctccatcatg    180
atgtattttc tgctgggaat cacactcctg cgctcataca tgcagagcgt gtggaccgaa    240
gagtctcaat gcaccttgct gaatgcgtcc atcacgaaa catttaaytg ctccttcagc     300
tgtggtccag actgctggaa actttctcag tacccctgcc tccaggtgta cgttaacctg    360
acttcttccg ggaaaaagct cctcctctac cacacagaag agacaataaa atcaatcag    420 aagtgctcct atatacctaa atgtggaaaa aattttgaag aatccatgtc cctggtgaat    480
gttgtcatgg aaaacttcag gaagtatcaa cacttctcct gctattctga cccagaagga    540
aaccagaaga gtgttatcct aacmaaactc tacagttcca acgtgctgtt ccattcactc    600
ttctggccaa cctgtatgat ggctgggggt gtggcaattg ttgccatggt gaaacttaca    660
cagtacctct ccctactatg tgagaggatc cacggatcaa tagataa                  707
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:primer to
    amplify BK beta 2

<400> SEQUENCE: 7
atgacagcct ttcctgcctc agggaag                                27

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:primer to
    amplify BK beta 2

<400> SEQUENCE: 8
agatttctct gctcttcctt tgctcctcc                              29

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:primer to
    amplify BK beta 2

<400> SEQUENCE: 9
ggctggctgg actgtagaag catg                                   24

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:primer to
    amplify BK beta 2

<400> SEQUENCE: 10
gaggctgtcc agataaatcc caagtgc                                27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:primer to
    amplify BK beta 2

<400> SEQUENCE: 11
ggactgagaa gcccatcatg gcaaacc                                27

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:primer to
    amplify BK beta 3

<400> SEQUENCE: 12
atggcgaagc tccgggtggc ttac                                   24

```
<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:primer to
      amplify BK beta 3

<400> SEQUENCE: 13
ttaagagaac ttgcgcttct tcatgg                                         26

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:primer to
      amplify BK beta 3

<400> SEQUENCE: 14
gatgtgcttc tgcatcgcac tcatg                                          25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:primer to
      amplify BK beta 2

<400> SEQUENCE: 15
aagatgtcga tatggaccag tggcc                                          25

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence:primer to
      amplify BK beta 2

<400> SEQUENCE: 16
ttatctattg atccgttgga tcctctc                                        27

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:primer to
      amplify BK beta 2

<400> SEQUENCE: 17
ctccttcagc tgtcctccag actgc                                          25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:primer to
      amplify BK beta 4

<400> SEQUENCE: 18
gtcccagtag aatagctcgg tcctc                                          25
```

```
<210> SEQ ID NO 19
<211> LENGTH: 191
<212> TYPE: PRT
<213> ORGANISM: Homo sapiens
<220> FEATURE:
<223> OTHER INFORMATION: BK beta 1

<400> SEQUENCE: 19

Met Val Lys Lys Leu Val Met Ala Gln Lys Arg Gly Glu Thr Arg Ala
 1               5                  10                  15

Leu Cys Leu Gly Val Thr Met Val Val Cys Ala Val Ile Thr Tyr Tyr
                20                  25                  30

Ile Leu Val Thr Thr Val Leu Pro Leu Tyr Gln Lys Ser Val Trp Thr
            35                  40                  45

Gln Glu Ser Lys Cys His Leu Ile Glu Thr Asn Ile Arg Asp Gln Glu
        50                  55                  60

Glu Leu Lys Gly Lys Lys Val Pro Gln Tyr Pro Cys Leu Trp Val Asn
65                  70                  75                  80

Val Ser Ala Ala Gly Arg Trp Ala Val Leu Tyr His Thr Glu Asp Thr
                85                  90                  95

Arg Asp Gln Asn Gln Gln Cys Ser Tyr Ile Pro Gly Ser Val Asp Asn
            100                 105                 110

Tyr Gln Thr Ala Arg Ala Asp Val Glu Lys Val Arg Ala Lys Phe Gln
        115                 120                 125

Glu Gln Gln Val Phe Tyr Cys Phe Ser Ala Pro Arg Gly Asn Glu Thr
    130                 135                 140

Ser Val Leu Phe Gln Arg Leu Tyr Gly Pro Gln Ala Leu Leu Phe Ser
145                 150                 155                 160

Leu Phe Trp Pro Thr Phe Leu Leu Thr Gly Gly Leu Leu Ile Ile Ala
                165                 170                 175

Met Val Lys Ser Asn Gln Tyr Leu Ser Ile Leu Ala Ala Gln Lys
                180                 185                 190
```